(12) United States Patent
Gangwar et al.

(10) Patent No.: US 7,847,105 B2
(45) Date of Patent: Dec. 7, 2010

(54) METHODS AND COMPOUNDS FOR PREPARING CC-1065 ANALOGS

(75) Inventors: Sanjeev Gangwar, San Mateo, CA (US); Qian Zhang, San Ramon, CA (US)

(73) Assignee: Medarex, Inc., Princeton, NJ (US)

( * ) Notice: Subject to any disclaimer, the term of this patent is extended or adjusted under 35 U.S.C. 154(b) by 192 days.

(21) Appl. No.: 12/090,445

(22) PCT Filed: Oct. 18, 2006

(86) PCT No.: PCT/US2006/060050

§ 371 (c)(1),
(2), (4) Date: Apr. 16, 2008

(87) PCT Pub. No.: WO2007/051081

PCT Pub. Date: May 3, 2007

(65) Prior Publication Data

US 2008/0281102 A1    Nov. 13, 2008

Related U.S. Application Data

(60) Provisional application No. 60/730,804, filed on Oct. 26, 2005.

(51) Int. Cl.
*C07D 209/56* (2006.01)
(52) U.S. Cl. .................................................. 548/427
(58) Field of Classification Search .................. 548/427; 514/411
See application file for complete search history.

(56) References Cited

U.S. PATENT DOCUMENTS

| | | | |
|---|---|---|---|
| 4,169,888 A | 10/1979 | Hanka et al. |
| 4,391,904 A | 7/1983 | Litman et al. |
| 4,671,958 A | 6/1987 | Rodwell et al. |
| 4,816,567 A | 3/1989 | Cabilly et al. |
| 4,912,227 A | 3/1990 | Kelly et al. |
| 4,923,990 A | 5/1990 | Nakano et al. |
| 4,952,394 A | 8/1990 | Senter |
| 4,975,278 A | 12/1990 | Senter et al. |
| 4,978,757 A | 12/1990 | Kelly et al. |
| 4,994,578 A | 2/1991 | Ohba et al. |
| 5,037,993 A | 8/1991 | Ohba et al. |
| 5,070,092 A | 12/1991 | Kanda et al. |
| 5,084,468 A | 1/1992 | Saito et al. |
| 5,101,038 A | 3/1992 | Nakano et al. |
| 5,117,006 A | 5/1992 | Saito et al. |
| 5,137,877 A | 8/1992 | Kaneko et al. |
| 5,138,059 A | 8/1992 | Takahashi et al. |
| 5,147,786 A | 9/1992 | Feng et al. |
| 5,176,996 A | 1/1993 | Hogan et al. |
| 5,187,186 A | 2/1993 | Kanda et al. |
| 5,223,409 A | 6/1993 | Ladner et al. |
| 5,225,539 A | 7/1993 | Winter |
| 5,288,514 A | 2/1994 | Ellman |
| 5,324,483 A | 6/1994 | Cody et al. |
| 5,332,740 A | 7/1994 | Saito et al. |
| 5,332,837 A | 7/1994 | Kelly et al. |
| 5,334,528 A | 8/1994 | Stanker et al. |
| 5,403,484 A | 4/1995 | Ladner et al. |
| 5,427,908 A | 6/1995 | Dower et al. |
| 5,475,092 A | 12/1995 | Chari et al. |
| 5,495,009 A | 2/1996 | Matteucci et al. |
| 5,530,101 A | 6/1996 | Queen et al. |
| 5,545,806 A | 8/1996 | Lonberg et al. |
| 5,547,667 A | 8/1996 | Angelucci et al. |
| 5,569,825 A | 10/1996 | Lonberg et al. |
| 5,571,698 A | 11/1996 | Ladner et al. |
| 5,573,922 A | 11/1996 | Hoess et al. |
| 5,580,717 A | 12/1996 | Dower et al. |
| 5,585,089 A | 12/1996 | Queen et al. |
| 5,585,499 A | 12/1996 | Chari et al. |
| 5,587,161 A | 12/1996 | Burke et al. |
| 5,606,017 A | 2/1997 | Willner et al. |
| 5,622,929 A | 4/1997 | Willner et al. |
| 5,625,126 A | 4/1997 | Lonberg et al. |
| 5,629,430 A | 5/1997 | Terashima et al. |
| 5,633,425 A | 5/1997 | Lonberg et al. |
| 5,641,780 A | 6/1997 | Amishiro et al. |
| 5,660,829 A | 8/1997 | Burke et al. |
| 5,661,016 A | 8/1997 | Lonberg et al. |
| 5,686,237 A | 11/1997 | Al-Bayati |
| 5,693,762 A | 12/1997 | Queen et al. |
| 5,703,080 A | 12/1997 | Nakakura et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,739,350 A | 4/1998 | Kelly et al. |
| 5,770,429 A | 6/1998 | Lonberg et al. |
| 5,773,001 A | 6/1998 | Hamann et al. |
| 5,773,435 A | 6/1998 | Kadow et al. |
| 5,786,377 A | 7/1998 | Garcia et al. |
| 5,786,486 A | 7/1998 | Fukuda et al. |
| 5,789,650 A | 8/1998 | Lonberg et al. |
| 5,814,318 A | 9/1998 | Lonberg et al. |

(Continued)

FOREIGN PATENT DOCUMENTS

EP    0786252 A1    7/1997

(Continued)

OTHER PUBLICATIONS

Ellis, et al., Metal cation complexation and activation of reverses CPyI analogues of CC-1065 and duocarmycin SA: partitioning the effects of binding and catalysis, J. of the Am. Chem. Soc. 123(38), 9299-9306 (2001).*

(Continued)

*Primary Examiner*—James O Wilson
*Assistant Examiner*—Erich A Leeser
(74) *Attorney, Agent, or Firm*—Lahive & Cockfield, LLP; Jane E. Remillard; Brian C. Trinque

(57) ABSTRACT

A method of forming a CBI CC-1065 analog utilizes NH2 as a starting material, where R3 is H or alkyl and R6 is H, substituted or unsubstituted lower alkyl, cyano, or alkoxy. Intermediates (I) are used and are claimed.

15 Claims, 3 Drawing Sheets

U.S. PATENT DOCUMENTS

| | | | |
|---|---|---|---|
| 5,846,545 | A | 12/1998 | Chari et al. |
| 5,874,299 | A | 2/1999 | Lonberg et al. |
| 5,877,296 | A | 3/1999 | Hamann et al. |
| 5,877,397 | A | 3/1999 | Lonberg et al. |
| 5,885,793 | A | 3/1999 | Griffiths et al. |
| 5,939,598 | A | 8/1999 | Kucherlapati et al. |
| 5,962,216 | A | 10/1999 | Trouet et al. |
| 5,969,108 | A | 10/1999 | McCafferty et al. |
| 5,985,908 | A * | 11/1999 | Boger ........................ 514/410 |
| 6,060,608 | A * | 5/2000 | Boger ........................ 548/420 |
| 6,066,742 | A | 5/2000 | Fukuda et al. |
| 6,075,181 | A | 6/2000 | Kucherlapati et al. |
| 6,103,236 | A | 8/2000 | Suzawa et al. |
| 6,114,598 | A | 9/2000 | Kucherlapati et al. |
| 6,130,237 | A | 10/2000 | Denny et al. |
| 6,132,722 | A | 10/2000 | Siemers et al. |
| 6,143,901 | A | 11/2000 | Dervan |
| 6,150,584 | A | 11/2000 | Kucherlapati et al. |
| 6,162,963 | A | 12/2000 | Kucherlapati et al. |
| 6,172,197 | B1 | 1/2001 | McCafferty et al. |
| 6,180,370 | B1 | 1/2001 | Queen et al. |
| 6,194,612 | B1 | 2/2001 | Boger et al. |
| 6,214,345 | B1 | 4/2001 | Firestone et al. |
| 6,262,271 | B1 | 7/2001 | Boger |
| 6,281,354 | B1 | 8/2001 | Boger |
| 6,310,209 | B1 | 10/2001 | Boger |
| 6,329,497 | B1 | 12/2001 | Boger |
| 6,342,480 | B1 | 1/2002 | Trouet et al. |
| 6,486,326 | B2 | 11/2002 | Boger |
| 6,512,101 | B1 | 1/2003 | King et al. |
| 6,521,404 | B1 | 2/2003 | Griffiths et al. |
| 6,534,660 | B1 | 3/2003 | Yongxin et al. |
| 6,544,731 | B1 | 4/2003 | Griffiths et al. |
| 6,548,530 | B1 * | 4/2003 | Boger ........................ 514/410 |
| 6,555,313 | B1 | 4/2003 | Griffiths et al. |
| 6,555,693 | B2 | 4/2003 | Ge et al. |
| 6,559,125 | B1 * | 5/2003 | Dervan et al. ................. 514/12 |
| 6,566,336 | B1 | 5/2003 | Sugiyama et al. |
| 6,593,081 | B1 | 7/2003 | Griffiths et al. |
| 6,630,579 | B2 | 10/2003 | Chari et al. |
| 6,759,509 | B1 | 7/2004 | King et al. |
| 6,762,179 | B2 | 7/2004 | Cochran et al. |
| 6,884,869 | B2 | 4/2005 | Senter et al. |
| 6,897,034 | B2 | 5/2005 | Bebbington et al. |
| 6,946,455 | B2 | 9/2005 | Sugiyama et al. |
| 7,087,600 | B2 | 8/2006 | Ng et al. |
| 7,091,186 | B2 | 8/2006 | Senter et al. |
| 7,115,573 | B2 | 10/2006 | Pickford et al. |
| 7,129,261 | B2 | 10/2006 | Ng et al. |
| 7,214,663 | B2 | 5/2007 | Bebbington et al. |
| 7,223,837 | B2 | 5/2007 | De Groot et al. |
| 7,304,032 | B2 | 12/2007 | Bebbington et al. |
| 7,329,507 | B2 | 2/2008 | Pickford et al. |
| 2002/0082424 | A1 | 6/2002 | Boger |
| 2002/0142955 | A1 | 10/2002 | Dubois et al. |
| 2003/0050331 | A1 | 3/2003 | Ng et al. |
| 2003/0064984 | A1 | 4/2003 | Ng et al. |
| 2003/0073852 | A1 | 4/2003 | Ng et al. |
| 2003/0083263 | A1 | 5/2003 | Doronina et al. |
| 2003/0096743 | A1 | 5/2003 | Senter et al. |
| 2003/0130189 | A1 | 7/2003 | Senter et al. |
| 2004/0121940 | A1 | 6/2004 | De Groot et al. |
| 2005/0014700 | A1 | 1/2005 | Boger |
| 2005/0026987 | A1 | 2/2005 | Boger |
| 2005/0239713 | A1 | 10/2005 | Domling et al. |
| 2005/0249740 | A1 | 11/2005 | Domling et al. |
| 2005/0272798 | A1 | 12/2005 | Ng et al. |
| 2006/0229253 | A1 | 10/2006 | Doronina et al. |

FOREIGN PATENT DOCUMENTS

| | | |
|---|---|---|
| WO | WO-91/04753 | 4/1991 |
| WO | WO-96/10405 | 4/1996 |
| WO | WO-9712862 | 4/1997 |
| WO | WO-9745411 | 12/1997 |
| WO | WO-98/11101 | 3/1998 |
| WO | WO-98/25900 | 6/1998 |
| WO | WO-00/33888 | 6/2000 |
| WO | WO-0116104 | 3/2001 |
| WO | WO-01/83482 | 11/2001 |
| WO | WO-02/15700 | 2/2002 |
| WO | WO-02/096910 | 12/2002 |
| WO | WO 03/087055 * | 10/2003 |
| WO | WO-03086318 | 10/2003 |
| WO | WO-03087055 | 10/2003 |
| WO | WO-2004/032828 A | 4/2004 |
| WO | WO-2005112919 | 12/2005 |
| WO | WO-2006110476 | 10/2006 |

OTHER PUBLICATIONS

Patani, et al., Bioisoterism: A Rational Approach in Drug Design, Chem. Rev., 96, 3147-3176 (1996).*

Chang, et al., Strand Selective Cleavage of DNA by Diastereomers of Hairpin Polyamide-seco-CBI Conjugates, J. of the Am. Chem. Soc., 122(20), 4856-4864 (2000).*

Tercel, et al., Unsymmetrical DNA Cross-linking Agents: Combination of the CBI and PBD Pharmacophores, J. Med. Chem., 46, 2132-2151 (2003).*

Boger, et al., Synthesis and Evaluation of Duocarmycin and CC-1065 Analogues Containing Modifications in the Subunit Linking Amide, Journal of Organic Chemistry, 64(14), 5241-5244 (1999).*

Aristoff, Paul A. et al., "Synthesis and Biochemical Evaluation of the CBI-PDE-I-dimer, a Benzannelated Analog of (+)-CC-1065 That Also Produces Delayed Toxicity in Mice," J. Med. Chem., 1993, 36:1956-1963.

Boger, Dale L. et al., "1,2,9,9a-Tetrahydrocydopropa[c]-benz[e]indol-4-one (CBI) Analogs of CC-1065 and the Duocarmycins: Synthesis and Evaluation," 1995, 3(11): 1429-1453.

Boger, Dale L. et al., "CC-1065 and the Duocarmycins: Synthetic Studies," Chemical Reviews, 1997, 97(3):title page, 787-828.

Boger, Dale L. et al., "CC-1065 and the Duocarmycins: Understanding Their Biological Function Through Mechanistic Studies," Angew. Chem. Int. Ed. Engl. 1996, 35:title page, 1438-1474.

Boger, Dale L. et al., "DNA Alkylation Properties of the Duocarmycisn: (+)-Duocarmycin A, Epi-(+)-Duocarmycin A, Ent-(−)-Duocarmycin A and Epi,Ent-(−)-Duocarmycin A," Bioogranic & Medicinal Chemistry Letters, 1992, 2(7):759-765.

Boger, Dale L. et al., "Duocarmycin SA Shortened, Simplified, and Extended Agents: A Systematic Examination of the Role of the DNA Binding Subunit," J. Am. Chem. Soc., 1997, 119(21):4977-4986.

Boger, Dale L. et al., "Duocarmycin-Pyrindamycin DNA Alkylation Properties and Identification, Synthesis, and Evaluation of Agents Incorporating the Pharmacophore of the Duocarmycin-Pyrindamycin Alkylation Subunit. Identification of the CC-1065-Duocarmycin Common Pharmacophore," J. Am. Chem. Soc., 1990, 112:8961-8971.

Boger, Dale L. et al., "Isolation and Characterization of the Duocarmycin-Adenine DNA Adduct," J. Am. Chem. Soc., 1991, 113:6645-6649.

Boger, Dale L. et al., "Reversibility of the Duocarmycin A and SA DNA Alkylation Reaction," J. Am. Chem. Soc., 1993, 115:9872-9873.

Boger, Dale L. et al., "Synthesis and Preliminary Evaluation of (+)-CBI-Indole$_2$: An Enhanced Functional Analog of (+)-CC-1065," Bioorganic & Medicinal Chemistry Letters, 1991, 1(2):115-120.

Boger, Dale L. et al., "Synthesis and Preliminary Evaluation of Agents Incorporating the Pharmacophore of the Duocarmcin/Pyrindamycin Alkylation Subunit: Identification of the CC-1065/Duocarmycin Common Pharmacophore," 1990, 55:4499-4502.

Boger, Dale L. et al., "Synthesis of N-(tert-Butyloxycarbonyl)-CBI, CBI, CBI-CDPI₁, and CBI-CDPI₂:Enhanced Functional Analogues of CC-1065 Incorporating the 1,2,9,9a-Tetrahydrocyclopropa[c]benz[e]indol-4-one (CBI) Left-Hand Subunit," 1990, 55:5823-5832.

Boger, Dale L. et al., "Synthesis, Chemical Properties, and Preliminary Evaluation of Substituted CBI Analogs of CC-1065 and the Duocarmycins Incorporating the 7-Cyano-1,2,9,9a-tetrahydrocyclopropa[c]benz[e]indol-4-one Alkylation Subunit: Hammett Quantitation of the Magnitude of Electronic Effects on Functional Reactivity," J. Org. Chem., 1996, 61:4894-4912.

Carl, Philip L. et al., "A Novel Connector Linkage Applicable in Prodrug Design," Journal of Medicinal Chemistry, May 1981 (24)5:479-480.

Chari, Ravi V. J. et al., "Enhancement of the Selectivity and Antitumor Efficacy of a CC-1065 Analogue Through Immunoconjugate Formation," Cancer Res., Sep. 1995, 55:4079-4084.

Chau, Ying et al., "Synthesis and Characterization of Dextran-Peptide-Methotrexate Conjugates for Tumor Targeting via Mediation by Matrix Metalloproteinase II and Matrix Metalloproteinase IX," Bioconjugate Chem., 2004, 15:931-941.

de Groot, Franciscus M. H. et al., "Elongated Multiple Electronic Cascade and Cyclization Spacer Systems in Activatible Anticancer Prodrugs for Enhanced Drug Release," J. Org. Chem., 2001, 66(26):8815-8830.

de Groot, Franciscus M. H. et al., "Synthesis and Biological Evaluation of 2'-Carbamate-Linked and 2'-Carbonate-Linked Prodrugs of Paclitaxel: Selective Activation by the Tumor-Associated Protease Plasmin," Journal of Medicinal Chemistry, 2000, 43(16):3093-3102.

de Groot, Franciscus M. H. et al., "Synthesis and Biological Evaluation of Novel Produgs of Anthracyclins for Selective Activation by the Tumor-Associated Protease Plasmin," 1999, 42(25):5277-5283.

Dubowchik, Gene M. et al., "Cathepsin B-Sensitive Dipeptide Prodrugs. 2. Models of Anticancer Drugs Paclitaxel (Taxol®), Mitomycin C and Doxorubicin," Bioorganic & Medicinal Chemistry Letters, 1998, 8:3347-3352.

Fukuda, Yasumichi et al., "Novel Synthetic of Optically Active CC-1065, U-73,975(Adozelesin), U-80,244(Carzelesin), U-77,779(Bizelesin), KW-2189, and DU-86," Heterocycles, 1997, 45(12):2303-2308.

Hanka, L. J. et al., "CC-1065 (NSC-298223), A New Antitumor Antibiotic: Production, In Vitro Biological Activity, Microbiological Assays and Taxonomy of the Producing Microorganism," The Journal of Antibiotics, Dec. 1978, XXXI(12):1211-1217.

Hurley, Laurence H. et al., "Reaction of the Antitumor Antibiotic CC-1065 with DNA: Structure of a DNA Adduct with DNA Sequence Specificity," Science, Jul. 1984, 226:843-844.

Jonkman-De Vries, J. D. et al., "Systematic Study on the Chemical Stability of the Prodrug Antitumor Agent Carzelesin (U-80,244)," Journal of Pharmaceutical Sciences, Nov. 1996, 85(11):1227-1233.

Kline, Toni et al., "Novel Antitumor Prodrugs Designed for Activation by Matrix Metalloproteinases-2 and -9," Molecular Pharmaceutics, 2004, 1(1):9-22.

Kratz, Felix et al., "Development and In Vitro Efficacy of Novel MMP2 and MMP9 Specific Doxorubicin Albumin Conjugates," Bioorganic & Medicinal Chemistry Letters, 2001, 11:2001-2006.

Li L. H. et al., "Cytotoxicity and Antitumor Activity of Carzelesin, a Prodrug Cyclopropylpyrroloindole Analogue," Cancer Research, Sep. 1992, 52: 4904-4913.

Li, L. H. et al., "CC-1065 (NSC 298223), a Novel Antitumor Agent That Interacts Strongly with Double-stranded DNA," Cancer Research, 1982, 42:999-1004.

Martin, D. G. et al., "Structure of CC-1065 (NSC-298223), A New Antitumor Antibiotic," The Journal of Antibiotics, 1980, 33(8):902-903.

Martin, David G. et al., "CC-1065 (NSC 298223), A Potent New Antitumor Agent Improved Production and Isolation, Characterization and Antitumor Activity," The Journal of Antibiotics, 1981, 34(9):1119-1125.

Nagamura, Satoru et al., "Antitumor Antibiotics: Duocarmycins," Chemistry of Heterocyclic Compounds, 1998, 34(12):1386-1405.

Nagamura, Satoru et al., "Synthesis and Antitumor Activity of Duocarmycin Derivatives," Chem. Pharm. Bull., 1995, 43(9):1530-1535.

Nagamura, Satoru et al., "Synthesis and Antitumor Activity of Duocarmycin Derivatives: Modification of Segment A of Duocarmycin B2," Chem. Pharm. Bull., 1996, 44(9):1723-1730.

Petracek, F. J. et al., "Hydroxymethylketones as Pro-drugs," Annals of New York Academy of Sciences, 1987, 507:353-354.

Sun, Daekyu et al., "Structure-Activity Relationships of (+)-CC-1065 Analogues in the Inhibition of Helicase-Catalyzed Unwinding of Duplex DNA," Journal of Medicinal Chemistry, 1992, 35(10):1773-1782.

Swenson, David H. et al., "Mechanism of Interaction of CC-1065 (NSC 298223) with DNA," Cancer Research, Jul. 1982, 42:2821-2828.

Umemoto, Naoji et al., "Preparation and In Vitro Cytotoxicity of a Methotrexate-Anti-MM46 Monoclonal Antibody Conjugate Via an Oligopeptide Spacer," Int. J. Cancer, 1989, 43:677-684.

Warpehoski, M. A. et al., "Stereoelectronic Factors Influencing the Biological Activity and DNA Interaction of Synthetic Antitumor Agents Modeled on CC-1065," Journal of Medicinal Chemistry, 1988, 31: 590-603.

Hay, et al., "Structure-Activity Relationshipf for 4-Nitrobenzyl Carbamates of 5-Aminobenz(e)indoline Minor Groove Alkylating Agents as Prodrugs for GDEPT in Conjunction with E.coli Nitroreductase," J. Med. Chem., vol. 46, 2003. pp. 2456-2466.

Wang, et al., "Synthesis and preliminary cytotoxicity study of a cephalosporin-CC-1065 analogue prodrug," Chemical Biology, vol. 1, No. 4, 2001, pp. 1472-1476.

Townes, et al., "Investigation of a Novel Reductively-Activatable Anticancer Prodrug of SECO-CBI-TMI, An Analog of Duocarmycin SA," Med Chem Res, vol. 11, No. 4, 2002, pp. 248-253.

Tietze, et al., "Highly Selective Glycosylated Prodrugs of Cytostatic CC-1065 Analogues for Antibody-Directed Enzyme Tumor Therapy," Chembiochem, vol. 2, 2001, pp. 758-765.

Hay et al. "A 2-nitroimidazole carbamate prodrug of 5-amino-1-(chloromethyl)-3-[5,6,7-trimethoxyindol-2-yl)carbonyl]-1, 2-dihydro -3h-benz[e]indole (amino-seco-CBI-TMI) for use with ADEPT and GDEPT," Bioorganic & Medicinal Chemistry Letters, Oxford,GB, vol. 9, No. 15, Aug. 2, 1999, pp. 2237-2242. cited by other.

Wang, et al., "Synthesis and Preliminary Cytotoxicity Study of Glucuronide Derivatives of CC-1065 Analogues," Bioorganic & Medicinal Chemistry, vol. 11, 2003, pp. 1569-1575. cited by other.

Boger, Dale L. et al., "CBI Prodrug Analogs of CC-1065 and the Duocarmycins," Synthesis, No. SI:1505-1509 (1999).

* cited by examiner

METHODS AND COMPOUNDS FOR PREPARING CC-1065 ANALOGS

CROSS-REFERENCE TO RELATED APPLICATIONS

This application claims the benefit of U.S. Provisional Patent Application No. 60/730,804, filed Oct. 26, 2005, which is incorporated herein by reference in its entirety.

BACKGROUND

CC-1065 is known to be a potent cytotoxin. CC-1065 was first isolated from *Streptomyces zelensis* in 1981 by the Upjohn Company (Hanka et al., *J. Antibiot.* 31: 1211 (1978); Martin et al., *J. Antibiot.* 33: 902 (1980); Martin et al., *J. Antibiot.* 34: 1119 (1981)) and was found to have potent antitumor and antimicrobial activity both in vitro and in experimental animals (Li et al., *Cancer Res.* 42: 999 (1982)). CC-1065 binds to double-stranded B-DNA within the minor groove (Swenson et al., *Cancer Res.* 42: 2821 (1982)) with the sequence preference of 5'-d(A/GNTTA)-3' and 5'-d(AAAAA)-3' and alkylates the N3 position of the 3'-adenine by its CPI left-hand unit present in the molecule (Hurley et al., *Science* 226: 843 (1984)). Despite its potent and broad antitumor activity, CC-1065 cannot be used in humans because it causes delayed death in experimental animals.

Many analogs and derivatives of CC-1065 are known in the art. The research into the structure, synthesis and properties of many of the compounds has been reviewed. See, for example, Boger et al., *Angew. Chem. Int. Ed. Engl.* 35: 1438 (1996); and Boger et al., *Chem. Rev.* 97: 787 (1997).

A group at Kyowa Hakko Kogya Co., Ltd. has prepared a number of CC-1065 derivatives. See, for example, U.S. Pat. Nos. 5,101,038; 5,641,780; 5,187,186; 5,070,092; 5,703,080; 5,070,092; 5,641,780; 5,101,038; and 5,084,468; and published PCT application, WO 96/10405 and published European application 0 537 575 A1.

The Upjohn Company (Pharmacia Upjohn) has also been active in preparing derivatives of CC-1065. See, for example, U.S. Pat. Nos. 5,739,350; 4,978,757, 5,332,837 and 4,912,227.

BRIEF SUMMARY

One embodiment is a method of making a compound (I) or a salt thereof,

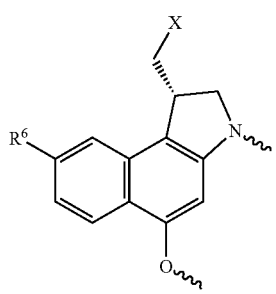

(I)

where $R^1$ and $R^2$ are each independently H, alkyl, —C(O)OR', —C(O)NR'R", or a protecting group, where R' and R" are independently selected from the group consisting of H, substituted alky, unsubstituted alkyl, substituted aryl, unsubstituted aryl, substituted heteroaryl, unsubstituted heteroaryl, substituted heterocycloalkyl, and unsubstituted heterocycloalkyl; $R^6$ is H, substituted or unsubstituted lower alkyl, cyano, or alkoxy; and X is halogen. In this method, protecting groups $R^{1'}$ and $R^{2'}$ are added to a compound (II)

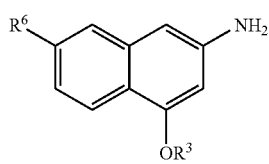

(II)

to form a compound (III)

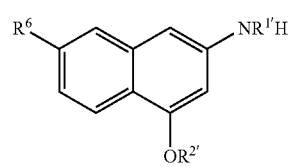

(III)

wherein $R^3$ is H or alkyl. A five membered ring is generated comprising the amine nitrogen of compound (III).

Another embodiment is a method of making a CBI CC-1065 analog, or a pharmaceutically acceptable salt thereof, having the following formula:

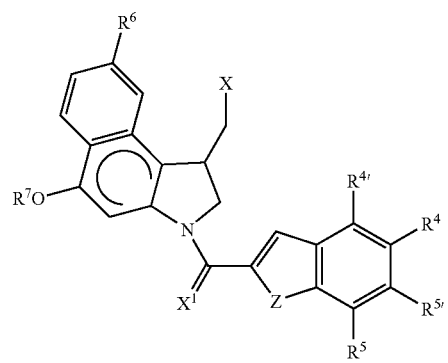

where X is halo;

$X^1$ and Z are each independently selected from O, S and $NR^8$, where $R^8$ is a member selected from H, substituted or unsubstituted alkyl, substituted or unsubstituted heteroalkyl, and acyl;

$R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^9R^{10}$, $NC(O)R^9$, $OC(O)NR^9R^{10}$, $OC(O)OR^9$, $C(O)R^9$, $SR^9$, $OR^9$, $CR^9$=$NR^{10}$, and $O(CH_2)_nNR^{11}R^{11'}$, where $R^9$ and $R^{10}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl or where $R^9$ and $R^{10}$ together with the nitrogen atom to which they are attached are optionally joined to form a substituted or unsubstituted heterocycloalkyl ring system having from 4 to 6 members, optionally containing two or more heteroatoms, and $R^{11}$ and $R^{11'}$ are each independently H or lower alkyl;

$R^6$ is H, substituted or unsubstituted lower alkyl, cyano, or alkoxy; and $R^7$ is a member selected from the group consisting of H, substituted alky, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, where $R^{12}$, $R^{13}$, and $R^{14}$ are members independently selected from H, substituted or unsubstituted alkyl, substituted or unsubstituted heteroalkyl and substituted or unsubstituted aryl, or where $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms.

The method includes adding protecting groups $R^{1'}$ and $R^{2'}$ to a compound (II)

(II)

[Structure: naphthalene with $R^6$, $NH_2$, $OR^3$ substituents]

to form a compound (III)

(III)

[Structure: naphthalene with $R^6$, $NR^{1'}H$, $OR^{2'}$ substituents]

where $R^3$ is H or alkyl. A five membered ring is generated comprising the amine nitrogen of compound (III). A binding unit is added to compound (III), the binding unit comprising

[Structure with $X^1$, $Z$, $R^{4'}$, $R^4$, $R^{5'}$, $R^5$]

Yet another embodiment is a compound of formula (I), or a pharmaceutically acceptable salt thereof:

(I)

[Structure with Br, $R^6$, $NR^1$, $OR^2$]

where $R^1$ and $R^2$ are each independently H, alkyl, —C(O)OR', —C(O)NR'R", or a protecting group, where R' and R" are independently selected from the group consisting of H, substituted alkyl, unsubstituted alkyl, substituted aryl, unsubstituted aryl, substituted heteroaryl, unsubstituted heteroaryl, substituted heterocycloalkyl, and unsubstituted heterocycloalkyl.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
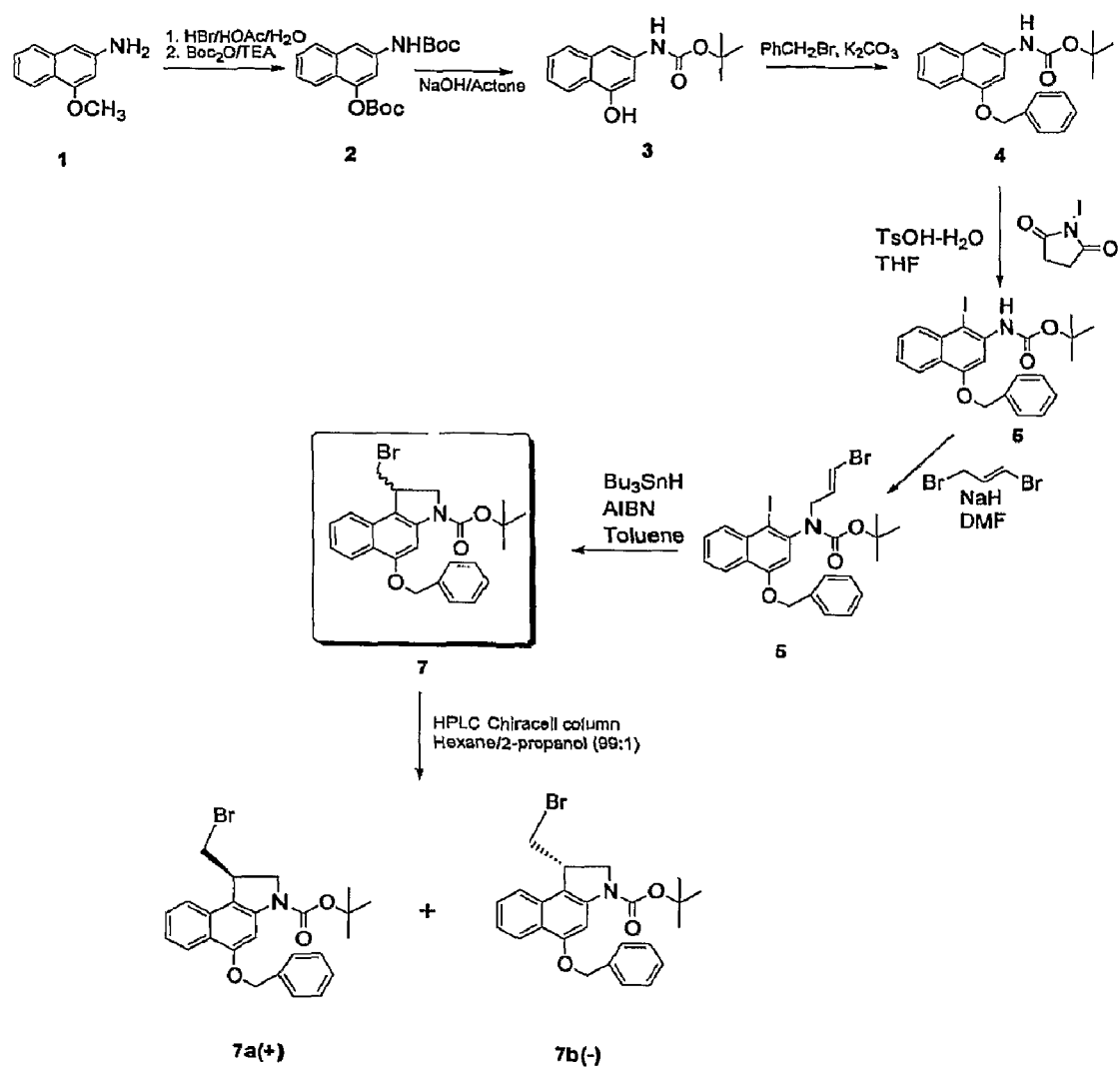
FIG. 1 is a synthetic scheme for one embodiment of a method of forming a CBI CC-1065 analog.

As used herein, "Boc" refers to t-butyloxycarbonyl.
"CPI" refers to cyclopropapyrroloindole.
"CBI" refers to cyclopropabenzindole.
"Cbz" is carbobenzoxy.
"DCM," refers to dichloromethane.
"DMF" is N,N-dimethylformamide.
"FMOC" refers to 9-fluorenylmethyloxycarbonyl.
"TEA" refers to triethylamine.
"THF" refers to tetrahydrofuran.
"EDC" refers to 1-(3-dimethylaminopropyl)-3-ethylcarbodiimide hydrochloride.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. The techniques and procedures are generally performed according to conventional methods in the art and various general references. The nomenclature used herein and the laboratory procedures in analytical chemistry, and organic synthetic described below are those well known and commonly employed in the art. Standard techniques, or modifications thereof, are used for chemical syntheses and chemical analyses.

The term "therapeutic agent" is intended to mean a compound that, when present in a therapeutically effective amount, produces a desired therapeutic effect on a mammal. For treating carcinomas, it is desirable that the therapeutic agent also be capable of entering the target cell.

The term "cytotoxin" is intended to mean a therapeutic agent having the desired effect of being cytotoxic to cancer cells. Cytotoxic means that the agent arrests the growth of, or kills, the cells.

The terms "prodrug" and "drug conjugate" are used herein interchangeably. Both refer to a compound that is relatively innocuous to cells while still in the conjugated form but which is selectively degraded to a pharmacologically active form by conditions, e.g., enzymes, located within or in the proximity of target cells.

The symbol $\sim\!\sim$ , whether utilized as a bond or displayed perpendicular to a bond indicates the point at which the displayed moiety is attached to the remainder of the molecule, solid support, substituent, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2 (butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of a number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene substituents, no orientation of the substituent is implied by the direction in which the formula of the substituent is written. For example, the formula —C(O)$_2$R'— represents both —C(O)$_2$R'— and —R'C(O)$_2$—.

The term "lower" in combination with the terms "alkyl" or "heteroalkyl" refers to a moiety having from 1 to 6 carbon atoms.

The terms "alkoxy," "alkylamino," "alkylsulfonyl," and "alkylthio" (or thioalkoxy) are used in their conventional sense, and refer to those alkyl groups attached to the remainder of the molecule via an oxygen atom, an amino group, an $SO_2$ group or a sulfur atom, respectively. The term "arylsulfonyl" refers to an aryl group attached to the remainder of the molecule via an $SO_2$ group, and the term "sulfhydryl" refers to an SH group.

In general, an "acyl" substituent is also selected from the group set forth above. As used herein, the term "acyl" substituent refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R'''' groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4, One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "diphosphate" includes but is not limited to an ester of phosphoric acid containing two phosphate groups. The term "triphosphate" includes but is not limited to an ester of phosphoric acid containing three phosphate groups. For example, particular drugs having a diphosphate or a triphosphate include:

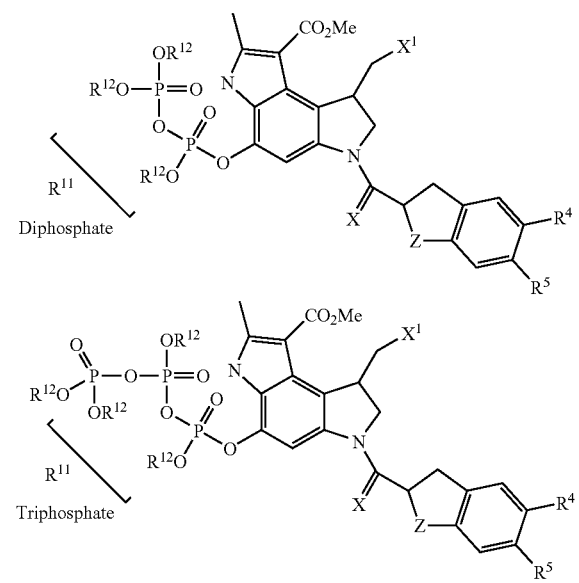

Diphosphate

Triphosphate

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

Regarding the term "protecting group," those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991. Examples of suitable protecting groups include, but are not limited to, BOC, FMOC, 2-trimethylsilylethoxycarbonyl, allyloxycarbonyl, 4-methyl-1-piperazinocarbonyl, 1-methyl-1-(4-biphenylyl)ethoxycarbonyl, diphenyloxycarbonyl, benzyl, t-butyl, tetrahydropyran, trimethylsilyl, t-butyldimethylsilyl, triisopropylsilyl, t-butyldiphenylsilyl, 2,2,2-trichloroethyl oxycarbonyl, diisopropylmethyl oxycarbonyl, vinyl oxycarbonyl, methoxy benzyl oxycarbonyl, nitrobenzyl oxycarbonyl, cyclohexyl oxycarbonyl, cyclopentyl oxycarbonyl, benzyloxycarbonyl, formyl, acetyl, trihaloacetyl, benzoyl, nitrophenylacetyl, 2-nitrobenzensulfonyl, phthalimido, and dithiasuccinoyl.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent. Pharmaceutically acceptable carriers include pharmaceutically acceptable salts, where the term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. These terms also encompass the term "antibody."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a precursor to arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH(NH$_2$)—CH$_3$, and so forth.

Amino acids and peptides may be protected by blocking groups. A blocking group is an atom or a chemical moiety that protects the N-terminus of an amino acid or a peptide from undesired reactions and can be used during the synthesis of a drug-cleavable substrate conjugate. It should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, hydrogen, D-amino acid, and carbobenzoxy (Cbz) chloride.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region ($V_H$) and a heavy chain constant region. The heavy chain constant region is comprised of three domains, $C_{H1}$, $C_{H2}$ and $C_{H3}$, and may be of the mu, delta, gamma, alpha or epsilon isotype. Each light chain is comprised of a light chain variable region ($V_L$) and a light chain constant region. The light chain constant region is comprised of one domain, $C_L$, which may be of the kappa or lambda isotype. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "antibody fragment" or "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antibody fragment" or "antigen-binding portion" of an antibody include (i) a Fab fragment, a monovalent fragment consisting of the $V_L$, $V_H$, $C_L$ and $C_{H1}$, domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The terms "monoclonal antibody" as used herein refers to a preparation of antibody molecules of single molecular composition. A monoclonal antibody composition displays a single binding specificity and affinity for a particular epitope.

"Solid support," as used herein refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. A solid support can also be a substrate, for example, a chip, wafer or well, onto which an individual, or more than one compound, of the invention is bound.

The compounds of the invention are prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al (eds.), VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

Cytotoxic analogs of CC-1065 can be formed using a cyclopropabenzindole (CBI) moiety as an alkylating unit instead of the cyclopropapyrrolloindole (CPI) moiety of CC-1065. As one example, CC-1065 CBI analogs include, but are not limited to compounds having the formula (or a pharmaceutically acceptable salt thereof):

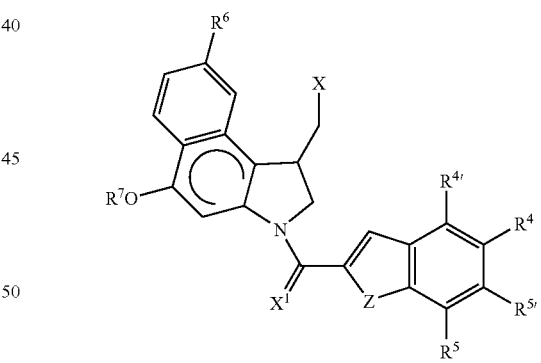

where X is halo. Preferably, X is Cl or Br and, more preferably, X is Br.

$X^1$ and Z are each independently selected from O, S and $NR^8$ where $R^8$ is a member selected from H, substituted or unsubstituted alkyl, substituted or unsubstituted heteroalkyl, and acyl.

$R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^9R^{10}$, $NC(O)R^9$, $OC(O)NR^9R^{10}$, $OC(O)OR^9$, $C(O)R^9$, $SR^9$, $OR^9$, $CR^9{=}NR^{10}$, and $O(CH_2)_nNR^{11}R^{11'}$, where $R^9$ and $R^{10}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, or where $R^9$ and $R^{10}$ together with the nitrogen atom to which they are attached are optionally joined to form a substituted or unsubstituted heterocycloalkyl ring system having from 4 to 6 members, optionally containing two or more heteroatoms, and $R^{11}$ and $R^{11'}$ are each independently H or lower alkyl.

$R^6$ is H, substituted or unsubstituted lower alkyl, cyano, or alkoxy. Preferably $R^6$ is methyl, cyano or H. More preferably, $R^6$ is H.

$R^7$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^2$ and $SiR^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, or where $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms.

Examples of CBI CC-1065 analogs are described in co-owned U.S. patent application Ser. Nos. 10/160,972; 10/161,233; 10/161,234, 11/134,685, and 11/134,826; all of which are incorporated herein by reference. These references also describe examples of synthesis and uses for these compounds. These compounds can be used as therapeutic agents (e.g., drugs) and as prodrugs. In at least some embodiments, the CBI CC-1065 analogs can be conjugated to targeting agents, such as an antibody, receptor, peptide, pectin, saccharide, nucleic acid or a combination thereof, for use in pharmaceutical compositions that selectively deliver the cytotoxic CBI CC-1065 analogs to desired target cells, such as carcinoma cells.

Representative examples of precancerous conditions that may be targeted by these compounds, include, but are not limited to: metaplasia, hyperplasia, dysplasia, colorectal polyps, actinic ketatosis, actinic cheilitis, human papillomaviruses, leukoplakia, lychen planus and Bowen's disease.

Representative examples of cancers or tumors that may be targeted by these compounds include, but are not limited to: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer and leukemias. It will be readily apparent to the ordinarily skilled artisan that the particular targeting agent can be chosen such that it targets the drug to the tumor tissue to be treated with the drug (i.e., a targeting agent specific for a tumor-specific antigen is chosen). Examples of such targeting agents are well known in the art, non-limiting examples of which include anti-Her2 for treatment of breast cancer, anti-CD20 for treatment of lymphoma, anti-PSMA for treatment of prostate cancer and anti-CD30 for treatment of lymphomas, including non-Hodgkin's lymphoma.

These compounds provide a method of killing a cell. The method includes administering to the cell an amount of a compound of the invention sufficient to kill said cell. In an exemplary embodiment, the compound is administered to a subject bearing the cell. In a further exemplary embodiment, the administration serves to retard or stop the growth of a tumor that includes the cell (e.g., the cell can be a tumor cell). For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

Pharmaceutical compositions include compositions wherein the active ingredient is contained in a therapeutically effective amount, i.e., in an amount effective to achieve its intended purpose. The actual amount effective for a particular application will depend, inter alia, on the condition being treated. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of diseases related to abnormal cellular proliferation, a circulating concentration of administered compound of about 0.001 μM to 20 μM is preferred, with about 0.01 μM to 5 μM being preferred. Patient doses for oral administration of the compounds described herein, typically range from about 1 mg/day to about 10,000 mg/day, more typically from about 10 mg/day to about 1,000 mg/day, and most typically from about 50 mg/day to about 500 mg/day.

Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 μmol/kg/day or less. For example, the patient doses can be 0.9, 0.6, 0.5, 0.45, 0.3, 0.2, 0.15, or 0.1 □mol/kg/day or less (referring to moles of the drug) of the drug or a drug conjugate, such as an antibody-drug conjugate. Preferably, the drug or drug conjugate growth of the tumor when administered in the daily dosage amount over a period of at least five days. In at least some embodiments, the tumor is a human-type tumor in a SCID mouse. As an example, the SCID mouse can be a CB17.SCID mouse (available from Taconic, Germantown, N.Y.).

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Generally, the CBI moiety has the formula:

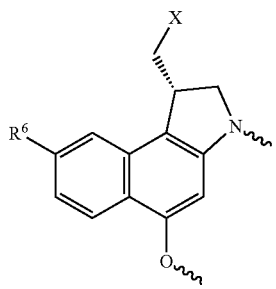

where substituents can be attached to the oxygen and nitrogen atoms, X is halo, and $R^6$ s H, substituted or unsubstituted lower alkyl, cyano, or alkoxy. Preferably, $R^6$ is H, methyl, or cyano. More preferably, $R^6$ is H. In addition, X is preferably Cl or Br and, more preferably, X is Br. Generally, a binding unit can be attached to the amine substituent of the CBI moiety. Examples of suitable binding units include, but are not limited to,

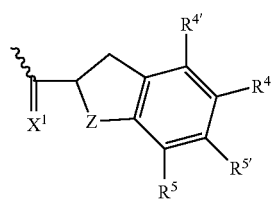

where $X^1$, Z, $R^4$, $R^4$, $R^5$, and $R^5$, are as defined above.

Examples of suitable binding units are illustrated and described in U.S. patent application Ser. Nos. 10/160,972; 10/161,233; 10/161,234, 11/134,685, and 11/134,826; as well as in U.S. Pat. No. 6,534,660, incorporated herein by reference. Suitable binding units within this formula also include binding units with multiple fused rings such as:

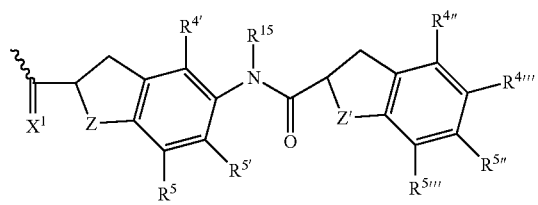

where Z' is independently selected from O, S and $NR^8$ where $R^8$ is a member selected from H, substituted or unsubstituted alkyl, substituted or unsubstituted heteroalkyl, and acyl.

$R^{4''}$, $R^{4'''}$, $R^{5''}$, and $R^{5'''}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^9R^{10}$, $NC(O)R^9$, $OC(O)NR^9R^{10}$, $OC(O)OR^9$, $C(O)R^9$, $SR^9$, $OR^9$, $CR^9=NR^{10}$, and $O(CH_2)_nNR^{11}R^{11'}$.

where $R^9$ and $R^{10}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, or where $R^9$ and $R^{10}$ together with the nitrogen atom to which they are attached are optionally joined to form a substituted or unsubstituted heterocycloalkyl ring system having from 4 to 6 members, optionally containing two or more heteroatoms, and $R^{11}$ and $R^{11'}$ are each independently H or lower alkyl.

$R^{15}$ can be H, substituted or unsubstituted alkyl, or $R^{15}$ and $R^{4'}$ or $R^{5'}$ can be combined to form a ring (e.g., a five- or six-membered ring.)

One intermediate compound useful in the formation of CC-1065 CBI analogs has the formula (I):

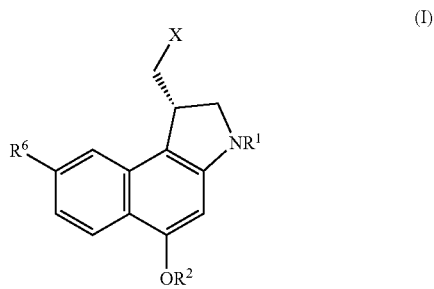

where $R^1$ and $R^2$ are each independently H, alkyl, —C(O)OR', —C(O)NR'R", or a protecting group, where R' and R" are independently selected from the group consisting of H, substituted alkyl, unsubstituted alkyl, substituted aryl, unsubstituted aryl, substituted heteroaryl, unsubstituted heteroaryl, substituted heterocycloalkyl, and unsubstituted heterocycloalkyl, and X is halogen.

In one conventional synthetic method for compound (I), the starting material is 1,3-dihydroxynaphthalene which is then reacted with ammonia in a pressurized chamber (e.g., a bomb) to replace the hydroxy group at the 3-position of the naphthalene with an amine.

Examples of this synthetic method can be found in U.S. Pat. No. 6,534,660 and D. L. Boger et al., J. Org. Chem. 57, 2873-2876 (1992), both of which are incorporated by reference. The amination reaction is followed by the addition of protecting groups to both the hydroxy and amine moieties.

Although the amination reaction may have acceptable yield on a small scale, it can be difficult to scale-up the reaction because of the use of a bomb to contain this pressurized reaction which typically occurs at a pressure substantially greater than 1 atmosphere (about $1.01 \times 10^5$ Pa) and generally at a pressure of at least 1.5 atmospheres ($1.52 \times 10^5$ Pa). This synthetic method has been found to result in a substantially lower yield when scaled-up.

Figure 2:
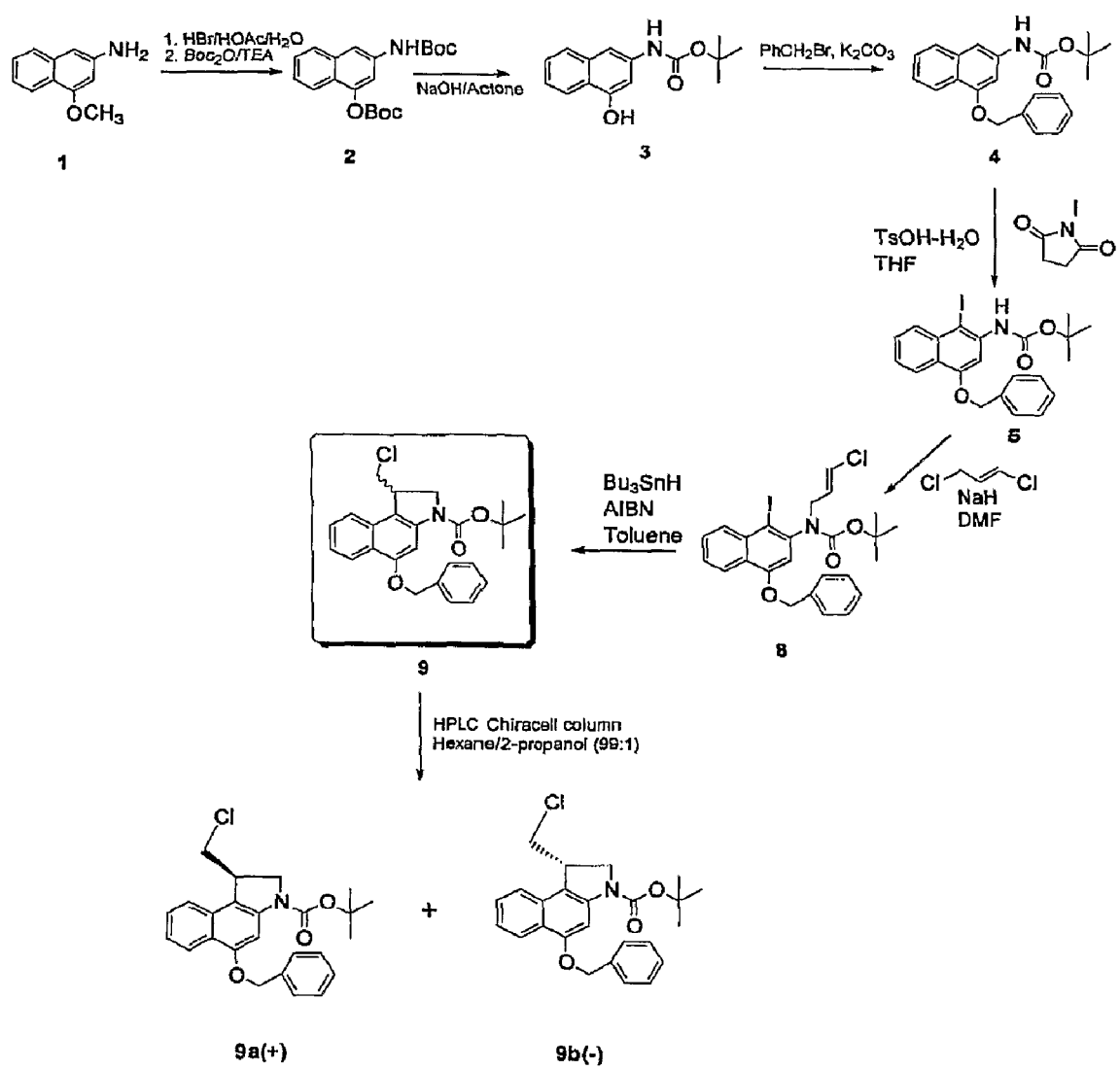
FIG. 2 is a synthetic scheme for another embodiment of a method of forming a CBI CC-1065 analog.

In contrast to the conventional methods, the starting material can be compound (II), as illustrated in the synthetic schemes of FIGS. 1 and 2:

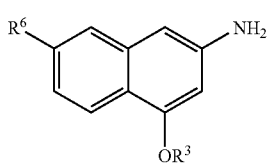

(II)

where $R^3$ is H or alkyl. Preferably, $R^3$ is $C_{1-5}$ alkyl and, more preferably, methyl. For example, 4-methoxy-2-naphthylamine is available commercially from Aldrich Chemical Company, Inc., Milwaukee, Wis. It is relatively easy to hydrolyze the compound, if $R^3$ is alkyl, and add protecting groups, $R^{1'}$, to both the hydroxy and amine moieties to form compound (III)

(III)

In some embodiments, as illustrated in FIGS. 1 and 2, it is desirable to provide different protecting groups on the amine and hydroxy functionalities. Accordingly, the initial protecting group, $R^{1'}$, can be removed from one of these moieties (e.g., from the hydroxy moiety) and replaced with a second, different protecting group, $R^{2'}$, to provide compound (IV)

(IV)

One specific example of compound (IV) has the formula:

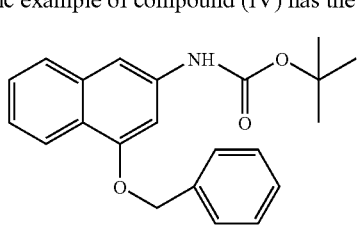

Having different protecting groups on the hydroxyl and amine substituents can facilitate later reaction steps where one of the protecting groups can be selectively removed while leaving the other protecting group. Alternatively, different protecting groups can be initially added to the hydroxyl and amine substituents.

Schemes 1 and 2 (FIGS. 1 and 2) illustrate one embodiment of the remaining steps in forming compound (I) from compound (IV). These steps can include, for example, forming a ring using the nitrogen of the amine group. This can be accomplished, for example, by alkylation of the aryl ring adjacent the nitrogen followed by a ring closure step. In one embodiment, iodination of compound (IV) by N-iodosuccinimide produces a compound which can then be alkylated using 1,3-dibromopropene or 1,3-dichloropropene. Ring closure can then be performed using tributyltin hydride in the presence of 2,2'-azobisisobutyronitrile (AIBN) to give the racemic CBI-derivative, compound (V):

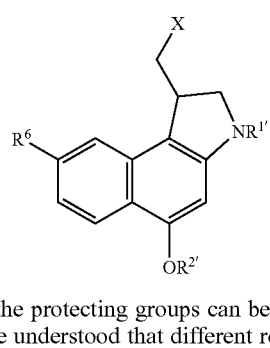

(V)

If desired, the protecting groups can be removed to form CBI. It will be understood that different reactants and catalysts can be used in these reaction steps. Examples can be found in Boger, Chemical Reviews, 97, 787-828 (1997) incorporated herein by reference.

The racemic CBI-derivative can be separated using known techniques of the separation of enantiomers including the use of chromatographic methods. One particularly useful technique is high pressure liquid chromatography (HPLC) using a chiral column. For example, separation of such enantiomers has been performed using a HPLC Chiralcel column and hexane/isopropanol (99:1) eluent to give compound (I).

Specific examples of Compound (I) include, but are not limited to,

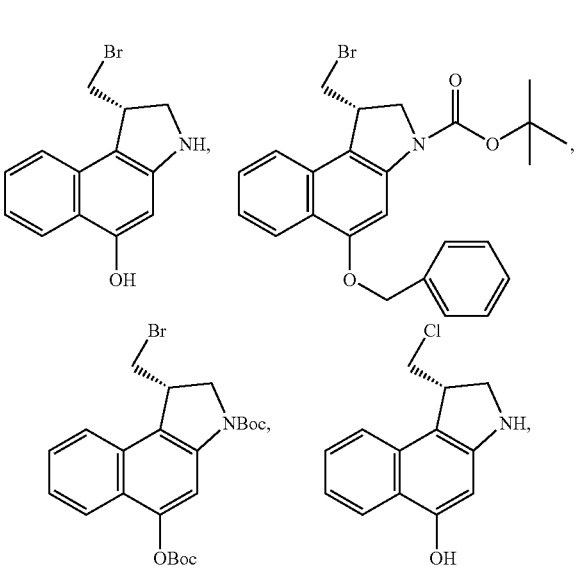

-continued

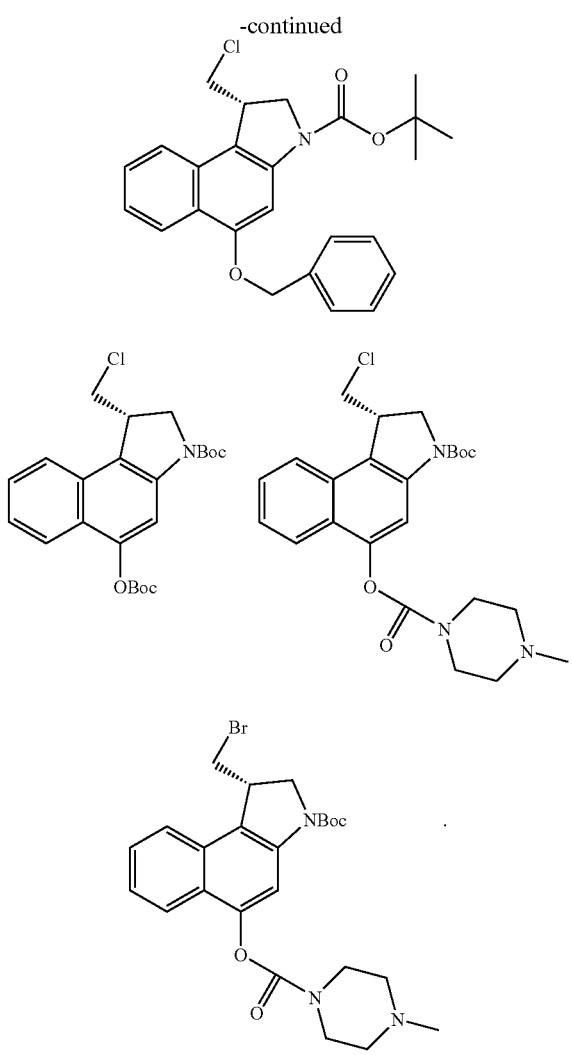

Compound (I) can be used to form CBI CC-1065 analogs as described, for example, in co-owned U.S. patent application Ser. Nos. 10/160,972; 10/161,233; 10/161,234, 11/134,685, and 11/134,826, all of which are incorporated herein by reference. For example, a binding unit can be added to Compound (I) by deprotecting the amine substituent and reacting a compound comprising the binding unit with the deprotected amine. Additional substituents can be added to the oxygen atom of the CBI compound by deprotecting the oxygen and reacting it with appropriate reactant(s).

EXAMPLES

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Example 1

Scheme 1 (FIG. 1)

Synthesis of N-(tert-butyloxycarbonyl)-4—O—(tert-butyloxycarbonyl)-2-naphthylamine (2)

A solution of 4-methoxy-2-naphthylamine (230 mg, 1.33 mmol) in glacial acetic acid (9.6 mL) and hydrobromic acid in water (16 mL, 48%) was refluxed under $N_2$ for 4 h. A small amount of sample (0.1 mL) was diluted with ethyl acetate (0.5 mL), and then water (0.5 mL) and TEA (0.1 mL) were added. TLC (20:1 DCM/methanol) of the organic layer showed no starting material and a new much lower spot ($R_f$=0.1). The solvent was removed under reduced pressure and the product was dried under vacuum to yield the intermediate 4-hydroxy-2-naphthylamine which was used for the next step without any purification. To a solution of 4-hydroxy-2-naphthylamine in dioxane (10 mL) was added TEA (1 mL) and di-tert-butyl dicarbonate (1.149 g, 5.27 mmol). The reaction mixture was refluxed under $N_2$ for 4 h. TLC (4:1 hexane/ethyl acetate) showed no starting material and a new higher spot ($R_f$=0.55). The reaction mixture was diluted with ethyl acetate (50 mL) and washed with water. The aqueous layer was extracted with ethyl acetate (2×50 mL) and the organics were combined and washed with brine. The organics were dried over anhydrous $Na_2SO_4$, filtered and concentrated under reduced pressure to yield N-(tert-butyloxycarbonyl)-4—O—(tert-butyloxycarbonyl)-2-naphthylamine (2, 80% yield) as oil.

Synthesis of Compound 3

To a solution of compound 2 in acetone (10 mL) was added NaOH solution in water (10 mL, 1 M). The reaction mixture was stirred at room temperature for overnight. TLC (4:1 hexane/ethyl acetate) showed no starting material and a new lower spot. The reaction mixture was extracted with ethyl acetate (50 mL) and washed with water. The aqueous layer was extracted with ethyl acetate (2×50 mL) and the organics were washed with brine, dried over anhydrous $Na_2SO_4$ and concentrated. The residue was purified on 10 g silica gel column with 10-20% ethyl acetate in hexane to yield compound 3 (181 mg, 53%) as an oil.

Synthesis of Compound 4

A solution of compound 3 (5 g, 19.3 mmol) in anhydrous DMF (50 ml) under nitrogen atmosphere was treated with benzyl bromide (4 g, 23.1 moles), potassium carbonate (3.7 g, 27 moles) and tetrabutylammonium iodide (70 mg, 0.01 mmoles). The reaction mixture was stirred at room temperature for 8 h. The reaction mixture was concentrated under reduced pressure. Chromatographic (4×10 cm $SiO_2$, 10-20% EtOAc-hexane gradient elution) separation provided pure compound 4 (5.48 g, 83%) as a cream powder. $^1$H NMR ($CDCl_3$, 400 MHz, ppm) 8.22 (d, 1H J=8.1 Hz, C5-H), 7.68 (d, 1H, J=8.2 Hz, C8-H), 7.3-7.5 (m, 8H, C1-H, C6-H, C7-H, $CH_2C_6H_5$), 7.06 (d, 1H, J=1.1 Hz, C3-H), 6.62 (br s, 1H, NH), 5.23 (S, 2H, $OCH_2(C_6H_5)$), 1.55 (s, 9H, $OC(CH_3)_3$).

Synthesis of Compound 5

To a 1000 ml round bottom flask equipped with a stir bar and a rubber septum was combined compound 4 (13 g, 0.0372 moles) and THF (300 ml). The clear yellow solution was cooled to −20 C with a dry ice bath under a nitrogen atmosphere. p-Toluenesulfonic acid (0.10 g, 0.0005 moles) was added to the reaction and the solution was stirred for 10 minutes. N-Iodosuccinimide (10 g, 0.0446 moles) was dissolved in THF (50 ml) and added to the reaction by cannula (approximately 1 hr). The solution was stirred in the ice bath for 2 hr and turned brownish. The solution was then removed from the ice bath and let warm to room temperature under nitrogen for 1.5 hr. TLC (2:1 hexane/DCM) showed no starting material and a new higher spot. The reaction was quenched with saturated $NaHCO_3$ (200 ml) and a white solid formed. After stirring the solution for 10 minutes, added EtOAc (200 ml) and water (100 ml) to the reaction. The aqueous layer was extracted with EtOAc (2×100 ml) and the organics were combined and extracted with brine (100 ml). The organics were dried over $MgSO_4$, filtered, and concentrated under vacuum to a dark red-brown solid. The solid was purified by column chromatography using 2:1 hexane/DCM as eluant to yield compound 5 (14 g, 79%) as a brown solid.

Synthesis of Compound 6

To a 500 ml round bottom flask equipped with stir bar and nitrogen inlet was combined compound 5 (22.5 g, 0.0473 moles) and anhydrous DMF (250 ml). The yellow-orange solution was cooled to 0° C. with an ice/salt bath under a nitrogen atmosphere. NaH (60%, 5.6 g, 0.146 moles) was added to the reaction in one portion. The solution turned cloudy and a gas was formed. The reaction was stirred in the ice bath for 15 minutes and then the ice bath was removed and the solution was stirred for another 15 minutes. cis/trans-1,3-Dibromopropene (14 ml, 0.14 moles) was added to the reaction in portions by syringe. The reaction was stirred under nitrogen at room temperature for 1 hr and turned a cloudy brown. The temperature rose to 40° C. The reactions was allowed to cool to room temperature. TLC (4:1 hexane/EtOAc) showed no starting material and a new lower spot. The reaction was quenched with water (500 ml). The aqueous layer was extracted with EtOAc (4×100 ml) and the organics were washed with brine (2×75 ml). The organics were dried over $MgSO_4$, filtered and concentrated under vacuum to a brown oil. The product was purified by column chromatography using 1:1 DCM/hexane as eluant to yield compound 6 (25 g, 89%) as a brown oil.

Synthesis of Compound 7

To a 1000 ml three necked round bottom flask equipped with stir bar, temperature probe, reflux condenser and nitrogen inlet was combined compound 6 (25 g, 0.0421 moles), toluene (500 ml), 2,2'-azobis(2-methylpropionitrile) (0.15 g, 0.0009 moles) and tributyltin hydride (3.4 ml, 0.0126 moles) [by syringe]. Nitrogen was bubbled through the solution for 15 minutes and then the reaction was heated to 80° C. under nitrogen. After heating at 80° C. for 15 minutes, tributyltin hydride (3.4 ml, 0.0126 moles) was added to the reaction by syringe. After heating for another 15 minute tributyltin hydride (3.4 ml, 0.0126 moles) was added to the reaction by syringe. After a further 15 minutes, tributyltin hydride (3.4 ml, 0.0126 moles) was added to the reaction by syringe. The total amount of tributyltin hydride added was 13.6 ml, 0.0505 moles. The reaction was heated at 80° C. for 30 minutes and then allowed to cool to room temperature. TLC (10% EtOAc/hexane) showed starting material and a new higher spot. The solution was concentrated under vacuum to a yellow solid. The solid was purified by column chromatography using as eluant 1:1 dichloromethane/hexane to give a yellow solid. The solid was recrystallized from hexane (200 ml, 45 C for 30 min, cooled in fridge for 2 hr, collected by filtration, dried under vacuum) to yield compound 7 (11.70 g, 59% yield) as a pale yellow solid.

NMR (1H, $CDCl_3$, 400 MHz): ☐ 1.61 (9H, s, C—$(CH_3)_3$); 3.30 (1H, t, J=26 Hz, CH—$CH_2$—N); 3.82 (1H, d, J=26 Hz, Br—$CH_2$—CH); 4.04 (1H, d, J=19 Hz, Br—$CH_2$—CH) 4.14 (1H, t, J=26 Hz, CH—$CH_2$—N); 4.21 (1H, m, $CH_2$—CH—$CH_2$); 5.26 (2H, s, O—$CH_2$—$C_6H_5$); 7.3-7.55 (8H, m, O—$CH_2$—$C_6H_5$, $C_{10}H_5$); 7.63 (1H, d, J=21 Hz, $C_{10}H_5$); 8.3 (1H, d, J=21 Hz, $C_{10}H_5$)

Resolution of Compound 7

The racemic compound 7 was dissolved in DCM (50 mg, 1 ml). The solution was then diluted with hexane (9 ml). The solution was then loaded onto a Chiralcel OD prep column (10 micron, 20×250 mm) and separated using hexane/isopropanol (99:1, 15 ml/min). The first enantiomer (7a) elutes from 10 to 15 min and the second enantiomers (7b) elutes from 17.5 to 25 min. The analytical column (Chiralcel OD, 0.46× 25 cm, 20 micrometers) gives a retention time of 7.71 min for 7a and 12.9 min for 7b (99:1 hexane/IPA, 1 ml/min, 15 minute run). NMR (1H, $CDCl_3$, 400 MHz): ☐ 1.61 (9H, s, C—$(CH_3)_3$); 3.30 (1H, t, J=26 Hz, CH—$CH_2$—N); 3.82 (1H, d, J=26 Hz, Br—$CH_2$—CH); 4.04 (1H, d, J=19 Hz, Br—$CH_2$—CH) 4.14 (1H, t, J=26 Hz, CH—$CH_2$—N); 4.21 (1H, m, $CH_2$—CH—$CH_2$); 5.26 (2H, s, O—$CH_2$—$C_6H_5$); 7.3-7.55 (8H, m, O—$CH_2$—$C_6H_5$, $C_{10}H_{15}$); 7.63 (1H, d, J=21 Hz, $C_{10}H_5$); 8.3 (1H, d, J=21 Hz, C $H_5$).

Example 2

Scheme 2 (FIG. 2)

The synthetic method procedure is as described above in Example 1 through the synthesis of compound 5.

Synthesis of Compound 8:

To a 250 ml round bottom flask equipped with stir bar and nitrogen inlet was combined compound 5 (8.4 g, 0.0177 moles) and anhydrous DMF (125 ml). The yellow-orange solution was cooled to 0° C. with an ice/salt bath under a nitrogen atmosphere. NaH (60%, 2.22 g, 0.0554 moles) was added to the reaction in one portion. The solution turned cloudy and a gas was formed. The reaction was stirred in the ice bath for 15 minutes and then the ice bath was removed and the solution was stirred for another 15 minutes. cis/trans-1,3-Dichloropropene (5.3 ml, 0.0571 moles) was added to the reaction in portions by syringe. The reaction was stirred under nitrogen at room temperature for 3 hr and turned a cloudy brown. TLC (4:1 hexane/EtOAc) showed no starting material and a new lower spot. The reaction was quenched with water (250 ml). The aqueous layer was extracted with EtOAc (3×100 ml) and the organics were washed with brine (2×50 ml). The organics were dried over $MgSO_4$, filtered and concentrated under vacuum to a brown oil. The product was purified by column chromatography using 1:1 DCM/hexane as eluant to yield (E/Z)-tert-butyl 4-(benzyloxy)-1-iodonaphthalene-2-yl(3-chloroallyl)carbamate (8) (9 g, 93%) as a yellow oil.

Synthesis of Compound 9:

To a 500 ml three necked round bottom flask equipped with stir bar, temperature probe, reflux condenser and nitrogen inlet was combined compound 8 (9 g, 0.0164 moles), toluene (200 ml), 2,2'-azobis(2-methylpropionitrile) (0.15 g, 0.0009 moles) and tributyltin hydride (1.5 ml, 0.0056 moles) [by syringe]. Nitrogen was bubbled through the solution for 15 minutes and then the reaction was heated to 80° C. under nitrogen. After heating at 80° C. for 15 minutes, tributyltin hydride (1.5 ml, 0.0056 moles) was added to the reaction by syringe. After heating for another 15 minute tributyltin hydride (1.5 ml, 0.0056 moles) was added to the reaction by syringe. After a further 15 minutes, tributyltin hydride (1.0 ml, 0.0037 moles) was added to the reaction by syringe. The total amount of tributyltin hydride added was 5.5 ml, 0.0204 moles. The reaction was heated at 80° C. for 30 minutes and then allowed to cool to room temperature. TLC (10% EtOAc/hexane) showed no starting material and a new higher spot. The solution was concentrated under vacuum to a yellow oil. The oil was purified by column chromatography using as eluant 100% Hexane to 5% EtOAc/Hexane to 10% EtOAc/Hexane to give a pale yellow solid. The solid was recrystallized from hexane (100 ml, 45 C for 30 min, cooled in fridge for 2 hr, collected by filtration, dried under vacuum) to yield compound 9 (4.16 g, 60% yield) as a white solid.

Resolution of Compound 9:

The racemic compound 9 was dissolved in DCM (50 mg, 1 ml). The solution was then diluted with hexane (9 ml). The solution was then loaded onto a Chiralcel OD prep column (10 micron, 20×250 mm) and separated using hexane/isopropanol (99:1, 15 ml/min). The first enantiomer (9a) elutes from 11.5 to 15 min and the second enantiomers (9b) elutes from 17.5 to 25 min. The analytical column (Chiralcel OD, 0.46× 25 cm, 20 microns) gives a retention time of 6.5 min for 9a and 10.6 min for 9b (99:1 hexane/IPA, 1 ml/min, 15 minute run). NMR (1H, $CDCl_3$, 400 MHz): d 1.61 (9H, s, C—$(CH_3)_3$); 3.44 (1H, t, J=25 Hz, CH—$CH_2$—N); 3.9-4.0 (2H, m, $C_1$—$CH_2$—CH); 4.12 (1H, t, J=26 Hz, CH—$CH_2$—N); 4.25 (1H, m, $CH_2$—$CH_2$); 5.26 (2H, s, O—$CH_2$—$C_6H_5$); 7.2-7.5 (8H, m, O—$CH_2$—$C_6H_5$, $C_{10}H_5$); 7.63 (1H, d, J=21 Hz, $C_{10}H_5$); 8.3 (1H, d, J=21 Hz, $C_{10}H_5$).

Example 3

Figure 3:
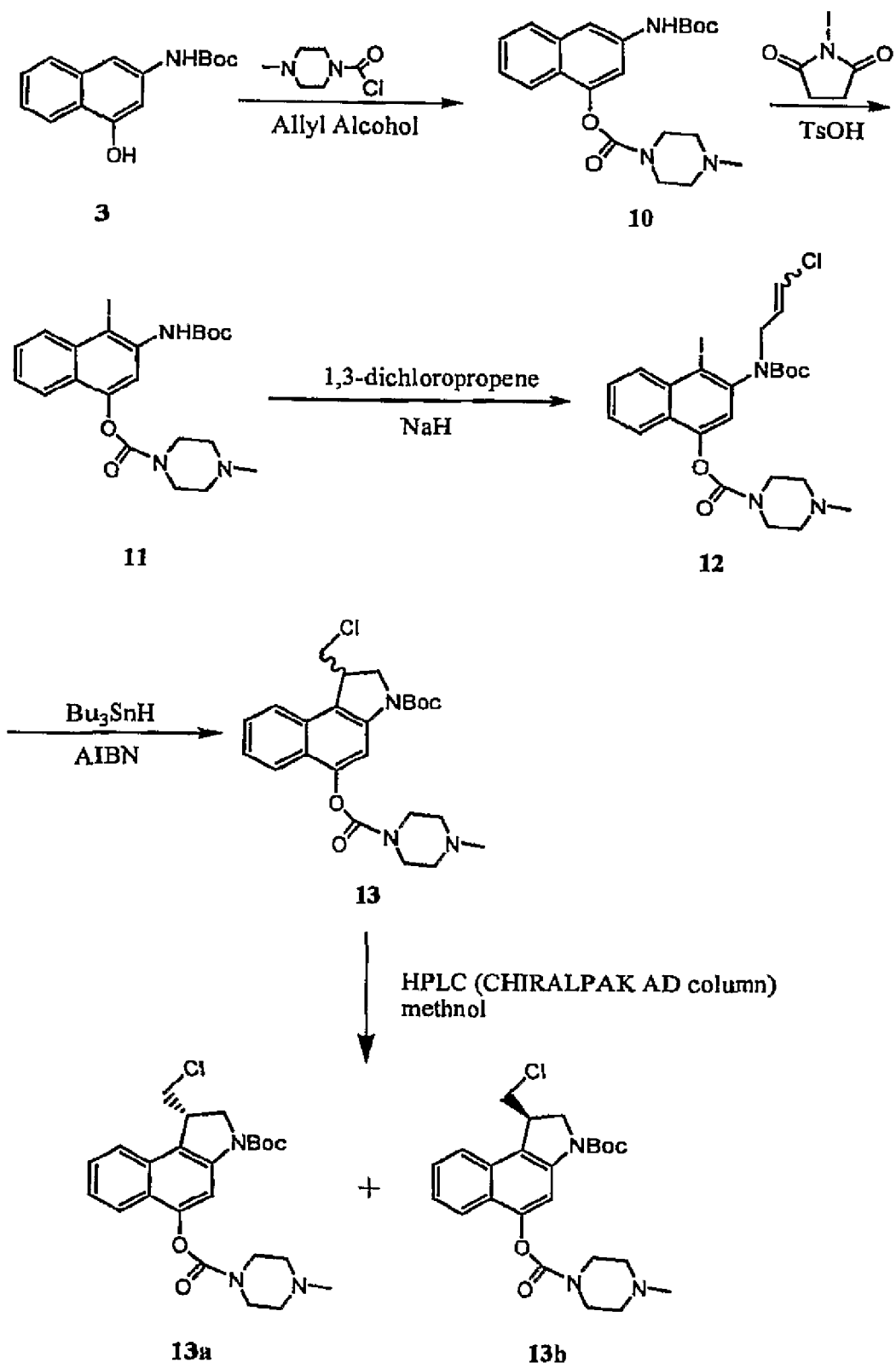
FIG. 3 is a synthetic scheme for a third embodiment of a method of forming a CBI CC-1065 analog.

Scheme 3 (FIG. 3)

The synthetic method procedure is as described above in Example 1 through the synthesis of compound 3.

Synthesis of Compound 10:

A solution of tert-butyl-4-hydroxynaphthalen-2-ylcarbamate (3) (500 mg, 2.89 mmol), 4-methyl-1-piperazinecarbonyl chloride hydrochloride (858 mg, 4.34 mmol), anhydrous pyridine (4.98 ml, 57.8 mmol), and allyl alcohol (4.98 ml, 73.2 mmol) in anhydrous DCM (20 ml) was stirred at room temperature for overnight. TLC (9:1 DCM/MeOH) showed no starting material and a much lower spot. The reaction mixture was quenched with water. The aqueous layer was extracted with EtOAc (3×50 ml) and the organics were washed with brine (2×50 ml). The organics were dried over $Na_2SO_4$, filtered and concentrated under vacuum to brown oil. The crude product was purified by column chromatography with 1-5% methanol in DCM to yield 10 (602 mg, 82%) as yellow solid.

$^1$HNMR (DMSO-$d_6$) δ 9.68 (s, 1H), 7.91 (s, 1H), 7.80 (d, 1H), 7.69 (s, 1H), 7.47 (t, 1H), 7.42 (t, 1H), 7.39 (t, 1H), 3.78 (s, 2H), 3.42 (s, 2H), 2.44 (s, 2H), 2.39 (s, 2H), 2.21 (s, 3H), 1.50 (s, 9H).

Synthesis of Compound 11:

Compound 10 (82 mg, 0.21 mmol), p-Toluenesulfonic acid (10 mg, 0.05 mmol), and N-iodosuccinimide (96 mg, 0.43 mmol) in anhydrous THF (5 ml) was stirred at room temperature overnight. TLC (9:1 DCM/MeOH) showed a small amount of starting material and a higher spot. The reaction mixture was quenched with saturated $NaHCO_3$ (10 ml). After stirring at room temperature for 10 min, the reaction mixture was extracted with EtOAc (3×20 ml) and the organics were washed with brine (2×20 ml). The organics were dried over $Na_2SO_4$, filtered and concentrated under vacuum to brown oil. The crude product was purified by column chromatography with 1-5% methanol in DCM to yield 11 (52 mg, 48%) as yellow oil.

$^1$HNMR (DMSO-$d_6$) δ 8.81 (s, 1H), 8.14 (d, 1H), 7.79 (d, 1H), 7.65 (t, 1H), 7.58 (t, 1H), 7.45 (t, 1H), 3.78 (s, 2H), 3.42 (s, 2H), 2.44 (s, 2H), 2.39 (s, 2H), 2.21 (s, 3H), 1.50 (s, 9H).

Synthesis of Compound 12:

A solution of compound 11 (102 mg, 0.2 mmol) in anhydrous DMF (5 ml) was cooled in an ice bath. Sodium hydride (60% in mineral oil, 32 mg, 0.8 mmol) was added to the reaction. The reaction mixture was stirred at 0° C. for 15 min and at room temperature for 15 min. cis/trans-1,3-Dichloroprepene (83.36 μl, 0.9 mmol) was added to the reaction. The reaction mixture was stirred at room temperature for 1 hr. TLC (9:1 DCM/MeOH) showed no starting material. The reaction mixture was quenched with water. The aqueous layer was extracted with EtOAc (3×10 ml) and the organics were washed with brine (2×10 ml). The organics were dried over $Na_2SO_4$, filtered and concentrated under vacuum to brown oil. The crude product was purified by column chromatography with 1-5% methanol in DCM to yield 12 (82 mg, 70%) as yellow solid.

$^1$HNMR (DMSO-$d_6$) δ 8.20 (d, 1H), 7.82 (d, 1H), 7.62 (m, 2H), 7.38 (d, 1H), 6.38 (m, 1H), 6.18 (m, 1H), 3.98-4.46 (dd, 2H), 3.78 (s, 2H), 3.42 (s, 2H), 2.44 (s, 2H), 2.39 (s, 2H), 2.21 (s, 3H), 1.50 (s, 9H).

Synthesis of Compound 13:

To a solution of 12 (82 mg, 0.14 mmol) in anhydrous toluene (3 ml), dry nitrogen was bubbled for 15 min. Tributyltin hydride (47.1 μl, 0.18 mmol) and 2,2'-azobisisobutyronitrile (10 mg, 0.06 mmol) were added to the reaction. The reaction mixture was heated at 80° C. for 15 min under nitrogen. TLC (9:1 DCM/MeOH) showed new blue spot and no starting material. The reaction mixture was concentrated under vacuum to yellow oil. The crude product was purified by column chromatography with 1-5% methanol in DCM to yield 13 (52 mg, 82%) as white solid.

$^1$HNMR (DMSO-$d_6$) δ 7.92 (d, 1H), 7.83 (m, 1H), 7.78 (d, 1H), 7.58 (t, 1H), 7.42 (t, 1H), 4.20 (m, 2H), 4.04 (m, 2H), 3.92 (m, 1H), 3.78 (s, 2H), 3.42 (s, 2H), 2.44 (s, 2H), 2.39 (s, 2H), 2.21 (s, 3H), 1.50 (s, 9H).

Resolution of Compound 13:

The racemic compound 13 is dissolved in methanol. The solution is then loaded onto a CHIRALPAK AD prep column (20 micron, 20×250 mm) and separated using methanol (15 ml/min). The first enantiomer (13a) elutes from 5.1 min and the second enantiomers (13b) elutes from 7.1 min. $^1$HNMR (DMSO-$d_6$) δ 7.92 (d, 1H), 7.83 (m, 1H), 7.78 (d, 1H), 7.58 (t, 1H), 7.42 (t, 1H), 4.20 (m, 2H), 4.04 (m, 2H), 3.92 (m, 1H), 3.78 (s, 2H), 3.42 (s, 2H), 2.44 (s, 2H), 2.39 (s, 2H), 2.21 (s, 3H), 1.50 (s, 9H).

Example 4
Synthesis of CBI CC-1065 Analog
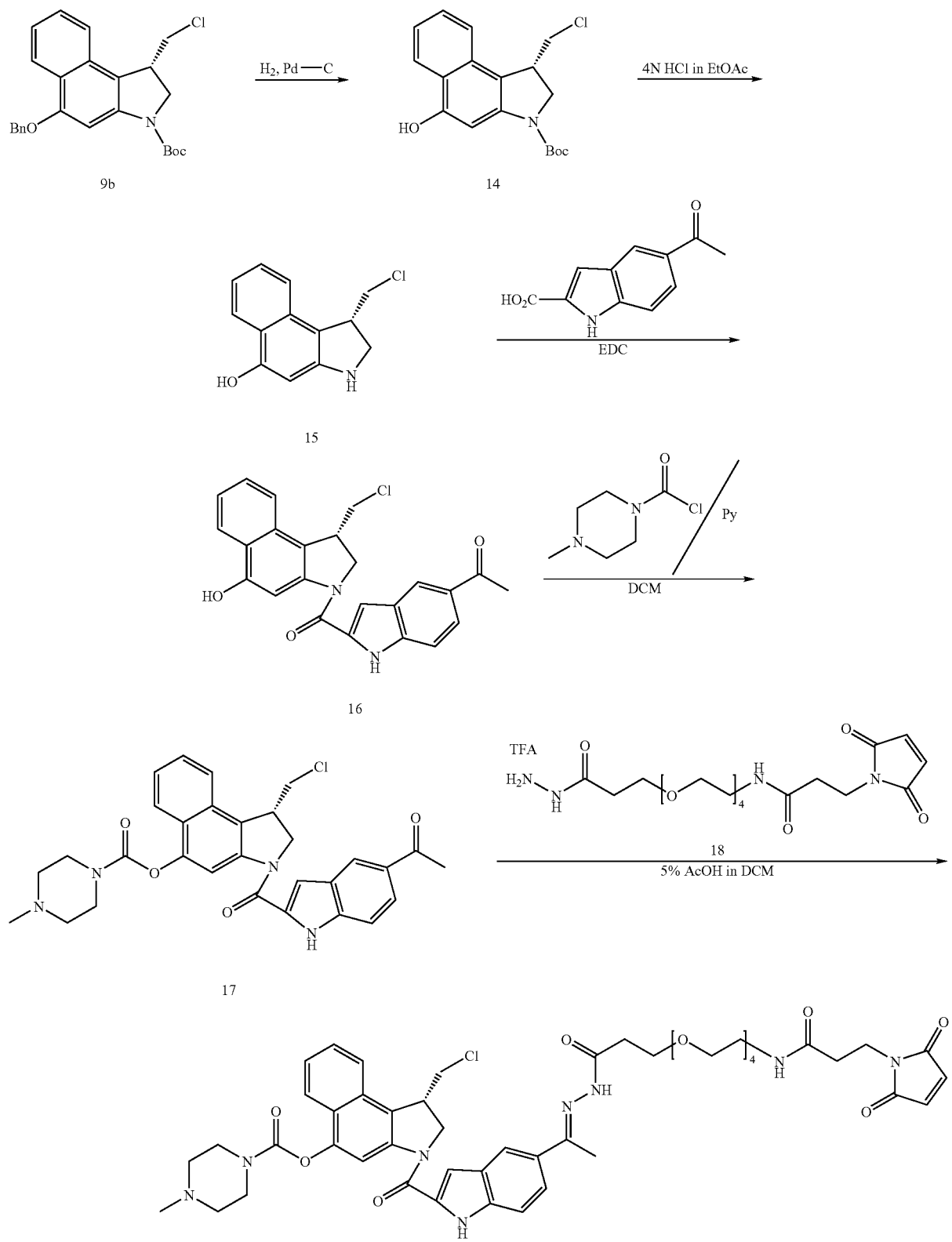

Synthesis of Compound (14). A solution of 9b (100 mg, 0.24 mmol) and 10% Pd—C (35 mg) in MeOH/CH$_2$Cl$_2$ (1/2, 10 ml) was degassed in vacuo for 40 s. The resulting mixture was placed under an atmosphere of hydrogen and stirred at 25° C. for 7 h. The reaction mixture was filtered through Celite (CH$_2$Cl$_2$ wash). The solvent was removed in vacuo. Chromatography on silica gel eluted with EtOAc/Hex (2/8) afforded 14 (77 mg, 98%). $^1$NMR DMSO-d$_6$) δ 10.36 (s, 1H), 8.04 (d, 1H, J=8.2 Hz), 7.72 (d, 1H, J=8.2 Hz), 7.61 (br s, 1H), 7.45 (t, 1H, J=8.4 Hz), 7.261 (t, 1H, J=8.4 Hz), 4.06 (m, 4H), 3.73 (m, 1H), 1.52 (s, 9H).

Synthesis of Compound (16). A solution of 14 (35 mg, 0.1 mmol) in 4 M HCl-EtOAc (5 ml) was stirred at 25° C. under Ar for 30 min. The solvent was removed in vacuo. To the residue was added 5-acetylindone-2-carboxylic acid (24.4 mg, 0.12 mmol). A solution of EDC (22.9 mg, 0.12 mmol) in DMF (3 ml) was added and the reaction mixture was stirred at 25° C. for 5 h. The solvent was removed. The crude product was chromatographed on silica gel eluted with 10% MeOH in CH$_2$Cl$_2$ to give 16 (40.7 mg, 93%). $^1$HNMR DMSO-d$_6$) δ12.13 (s, 1H), 10.47 (s, 1H), 8.45 (s, 1H), 8.10 (d, 1H, J=8.4 Hz), 7.96 (br s, 1H), 7.85 (d, 2H, J=8.4 Hz), 7.54 (d, 1H, J=8.4 Hz), 7.51 (t, 1H, J=8.2 Hz), 7.36 (t, 1H, J=7.6), 7.35 (s, 1H), 4.81 (t, 1H, 11.2 Hz), 4.54 (dd, 1H, 8.8 Hz), 4.23 (m, 1H), 4.01 (dd, 1H, J=10.2 Hz), 3.86 (dd, 1H, J=10.7 Hz), 2.61 (s, 3H).

Synthesis of Compound (17). 4-Methyl-1-piperazinecarbonyl chloride hydrochloride (19.9 mg, 0.1 mmol) was added to a solution of 16 (20 mg, 0.05 mmol) and anhydrous pyridine (25 μml, 0.3 mmol) in 3% allyl alcohol in dry methylene chloride (4 ml) and the mixture was stirred for 16 h. Purification of the crude product on silica gel yielded 17 (23.6 mg, 91%). $^1$NMR DMSO-d$_6$) δ 12.03 (s, 1H), 8.41 (s, 1H), 8.21 (s, 1H), 8.01 (d, 1H, J=8.4 Hz), 7.88 (d, 1H, J=8.4 Hz), 7.82 (dd, 1H, J=8.4 Hz), 7.58 (t, 1H, J=8.1 Hz), 7.51 (d, 1H, J=8.4 Hz), 7.46 (t, 1H, J=7.6 Hz), 7.37 (s, 1H), 4.86 (t, 1H, J=10.8 Hz), 4.57 (dd, 1H, J=10.8 Hz), 4.38 (m, 1H), 4.06 (dd, 1H, J=10.8 Hz), 3.86 (dd, 1H, J=11 Hz), 3.41 (br, 4H), 3.29 (br, 4H), 2.82 (s, 3H), 2.57 (s, 3H).

Synthesis of Compound (19). A solution of 17 (13 mg, 24 umol) and linker 18 (16.9 mg, 31 umol) in 5% acetic acid in dry methylene chloride (1 ml) was stirred for 30 min at 25° C. The solvent was completely removed in vacuo and purified by HPLC (SymmetryPrep C$^{18}$, 7 μm, 19×150 mm column) to give 19 (18.5 mg, 81%). MS: calcd for C$_{48}$H$_{57}$ClN$_8$O$_{11}$, (M+H) m/z 958.38, found 958.10.

Example 5

Proliferation Assays

The biological activity of the cytotoxic compounds of the invention can be assayed using the well established $^3$H-thymidine proliferation assay. This is a convenient method for quantitating cellular proliferation, as it evaluates DNA synthesis by measuring the incorporation of exogenous radiolabeled $^3$H-thymidine. This assay is highly reproducible and can accommodate large numbers of compounds.

To carry out the assay, promyelocytic leukemia cells, HL-60, are cultured in RPMI media containing 10% heat inactivated fetal calf serum (FCS). On the day of the study, the cells are collected, washed and resuspended at a concentration of 0.5×10$^6$ cells/ml in RPMI containing 10% FCS. 100 μl of cell suspension is added to 96 well plates. Serial dilutions (3-fold increments) of doxorubicin (as a positive control) or test compounds are made and 100 μl of compounds are added per well. Finally 10 μl of a 100 μCi/ml $^3$H-thymidine is added per well and the plates are incubated for 24 hours. The plates are harvested using a 96 well Harvester (Packard Instruments) and counted on a Packard Top Count counter. Four parameter logistic curves are fitted to the $^3$H-thymidine incorporation as a function of drug molarity using Prism software to determine IC$_{50}$ values.

The CBI CC-1065 analogs (e.g., compound 19 of Example 4) generally have an IC$_{50}$ value in the above assay of from about 1 pM to about 100 nM, preferably from about 10 p M to about 10 nM.

Example 6

Conjugation of Drug Molecules to Antibodies

This example describes reaction conditions and methodologies for conjugating a drug molecule of the invention (optionally including other groups, such as spacers, reactive functional groups and the like) to an antibody as a targeting agent. The conditions and methodologies are intended to be exemplary only and non-limiting. Other approaches for conjugating drug molecules to antibodies are known in the art.

The conjugation method described herein is based on introduction of free thiol groups to the antibody through reaction of lysines of the antibody with 2-iminothiolane, followed by reaction of the drug-linker molecule with an active maleimide group. Initially the antibody to be conjugated is buffer exchanged into 0.1M phosphate buffer pH 8.0 containing 50 mM NaCl, 2 mM DTPA, pH 8.0 and concentrated to 5-10 mg/ml. Thiolation is achieved through addition of 2-iminothiolane to the antibody. The amount of 2-iminothiolane to be added is determined in preliminary experiments and varies from antibody to antibody. In the preliminary experiments, a titration of increasing amounts of 2-iminothiolane is added to the antibody, and following incubation with the antibody for one hour at room temperature, the antibody is desalted into 50 mM HEPES buffer pH 6.0 using a Sephadex G-25 column and the number of thiol groups introduced determined rapidly by reaction with dithiodipyridine (DTDP). Reaction of thiol groups with DTDP results in liberation of thiopyridine which is monitored at 324 nm. Samples at a protein concentration of 0.5-1.0 mg/ml can be used. The absorbance at 280 nm is used to accurately determine the concentration of protein in the samples, and then an aliquot of each sample (0.9 ml) is incubated with 0.1 ml DTDP (5 mM stock solution in ethanol) for 10 minutes at room temperature. Blank samples of buffer alone plus DTDP are also incubated alongside. After 10 minutes, absorbance at 324 nm is measured and the number of thiols present quantitated using an extinction coefficient for thiopyridine of 19800M$^{-1}$.

Typically a thiolation level of three thiol groups per antibody is desired. For example, with one particular antibody this can be achieved through adding a 15 fold molar excess of 2-iminothiolane followed by incubation at room temperature for 1 hour. Antibody to be conjugated is therefore incubated with 2-iminothiolane at the desired molar ratio and then desalted into conjugation buffer (50 mM HEPES buffer pH 6.0 containing 5 mM glycine, 3% Glycerol and 2 mM DTPA). The thiolated material is maintained on ice whilst the number of thiols introduced is quantitated as described above.

After verification of the number of thiols introduced, the drug molecule containing an active maleimide group (e.g., compound 15 of Example 3) is added at a 3-fold molar excess per thiol. The conjugation reaction is carried out in conjugation buffer also containing a final concentration of 5% ethylene glycol dimethyl ether (or a suitable alternative solvent). Commonly, the drug stock solution is dissolved in 90% ethylene glycol dimethyl ether, 10% dimethyl sulfoxide. For addition to antibody, the stock solution is added directly to the thiolated antibody, which has enough ethylene glycol dimethyl ether added to bring the final concentration to 5%, or pre-diluted in conjugation buffer containing a final concentration of 10% ethylene glycol dimethyl ether, followed by addition to an equal volume of thiolated antibody.

The conjugation reaction is incubated at room temperature for 2 hours with mixing. Following incubation the reaction mix is centrifuged at 14000 RPM for 15 minutes and the pH can be adjusted to 7.2 if purification was not immediate. Purification of conjugate can be achieved through chromatography using a number of methods. Conjugate can be purified using size-exclusion chromatography on a Sephacryl S200 column pre-equilibrated with 50 mM HEPES buffer pH 7.2 containing 5 mM glycine, 50 mM NaCl and 3% glycerol. Chromatography can be carried out at a linear flow rate of 28 cm/h. Fractions containing conjugate can be collected, pooled and concentrated. Alternatively purification can be achieved through ion-exchange chromatography. Conditions vary from antibody to antibody and need to be optimized in each case. For example, antibody-drug conjugate reaction mix can be applied to an SP-Sepharose column pre-equilibrated in 50 mM HEPES, 5mM glycine, 3% glycerol, pH 6.0. The antibody conjugate can be eluted using a gradient of 0-1M NaCl in equilibration buffer. Fractions containing the conjugate can be pooled, the pH can be adjusted to 7.2 and the sample concentrated as required.

The entire disclosures of all applications, patents and publications, cited herein are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed as new and desired to be protected by Letters Patent of the United States is:

1. A method of making a compound (I) or a salt thereof,

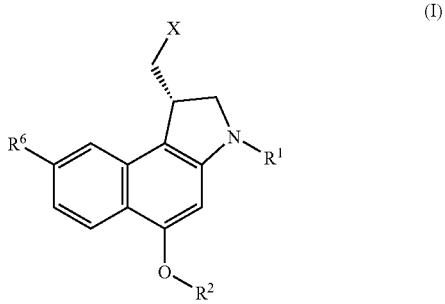

(I)

wherein $R^1$ and $R^2$ are each independently H, alkyl, —C(O)OR', —C(O)NR'R", or a protecting group, wherein R' and R" are independently selected from the group consisting of H, substituted alkyl, unsubstituted alkyl, substituted aryl, unsubstituted aryl, substituted heteroaryl, unsubstituted heteroaryl, substituted heterocycloalkyl, and unsubstituted heterocycloalkyl; $R^6$ is H, substituted or unsubstituted lower alkyl, cyano, or alkoxy; and X is halogen, the method comprising:

adding protecting groups $R^{1'}$ and $R^{2'}$ to a compound (II), wherein $R^{1'}$ and $R^{2'}$ are different protecting groups,

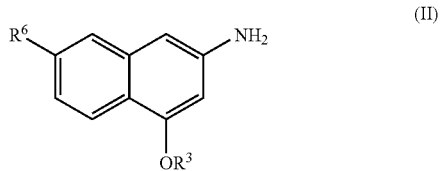

(II)

to form a compound (III)

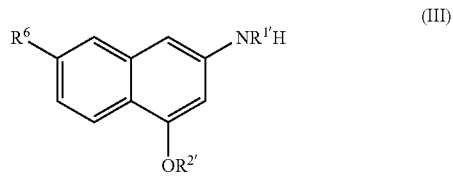

(III)

wherein $R^3$ is alkyl; and generating a five membered ring comprising the amine nitrogen of compound (III).

2. The method of claim 1, wherein $R^3$ is methyl.

3. The method of claim 1, wherein X is Cl or Br.

4. The method of claim 3, wherein X is Br.

5. The method of claim 1, wherein adding $R^{1'}$ and $R^{2'}$ comprises adding $R^{1'}$ to compound (II) to form compound (III')

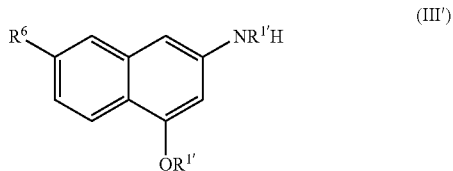

(III')

and replacing the protecting group $R^{1'}$ on the hydroxyl substituent with the protecting group $R^{2'}$.

6. The method of claim 1, wherein $R^{1'}$ is tert-butyloxycarbonyl.

7. The method of claim 6, wherein $R^{2'}$ is —CH$_2$Ph.

8. The method of claim 1 further comprising replacing $R^{1'}$ and $R^{2'}$ with hydrogen after generating the five membered ring.

9. The method of claim 1, wherein $R^{1'}$ and $R^1$ are the same and $R^{2'}$ and $R^2$ are the same.

10. The method of claim 1, wherein generating the five membered ring comprises iodination of a carbon adjacent the amine substituent of compound (III) followed by alkylation using 1,3-dihalopropene.

11. A method of making a CBI CC-1065 analog, or a pharmaceutically acceptable salt thereof, having the following formula:

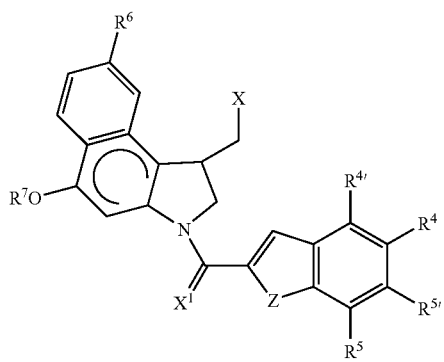

wherein X is halo;

X¹ and Z are each independently selected from O, S and NR⁸, wherein R⁸ is a member selected from H, substituted or unsubstituted alkyl, substituted or unsubstituted heteroalkyl, and acyl;

R⁴, R⁴', R⁵ and R⁵' are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, NO₂, NR⁹R¹⁰, NC(O)R⁹, OC(O)NR⁹R¹⁰, OC(O)OR⁹, C(O)R⁹, SR⁹, OR⁹, CR⁹=NR¹⁰, and OCH₂NR¹¹R¹¹';

wherein R⁹ and R¹⁰ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, or wherein R⁹ and R¹⁰ together with the nitrogen atom to which they are attached are optionally joined to form a substituted or unsubstituted heterocycloalkyl ring system having from 4 to 6 members, optionally containing two or more heteroatoms, and R¹¹ and R¹¹' are each independently H or lower alkyl;

R⁶ is H, substituted or unsubstituted lower alkyl, cyano, or alkoxy; and

R⁷ is a member selected from the group consisting of H, substituted alkyl, unsubstituted alkyl, substituted heteroalkyl, unsubstituted heteroalkyl, diphosphates, triphosphates, acyl, C(O)R¹²R¹³, C(O)OR¹², C(O)NR¹²R¹³, P(O)(OR¹²)₂, C(O)CHR¹²R¹³, SR¹² and SiR¹²R¹³R¹⁴, wherein R¹², R¹³, and R¹⁴ are members independently selected from H, substituted or unsubstituted alkyl, substituted or unsubstituted heteroalkyl and substituted or unsubstituted aryl, or wherein R¹² and R¹³ together with the nitrogen or carbon atom to which they are attached are optionally joined to form a substituted or unsubstituted heterocycloalkyl ring system having from 4 to 6 members, optionally containing two or more heteroatoms; the method comprising:

adding protecting groups R¹' and R²' to a compound (II), wherein R¹' and R²' are different protecting groups,

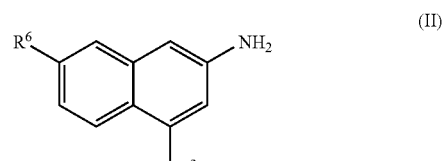

to form a compound (III)

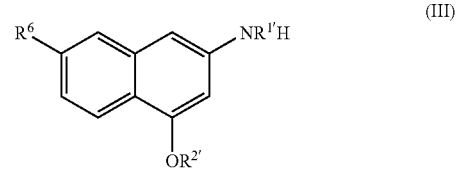

wherein R³ is alkyl; and generating a five membered ring comprising the amine nitrogen of compound (III) to make a compound (I);

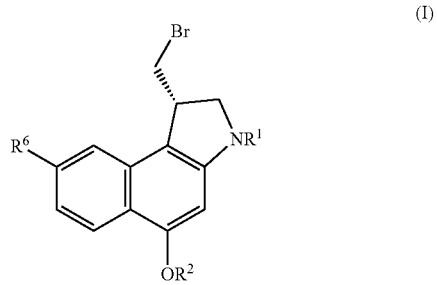

and adding a binding unit to compound (I), the binding unit comprising

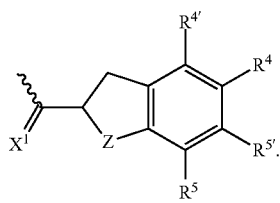

12. The method of claim 11, wherein generating the five membered ring comprises iodination of a carbon adjacent the amine substituent of compound (III) followed by alkylation using 1,3-dihalopropene prior to generating the five membered ring.

13. The method of claim 11, wherein adding the binding unit comprises removing the protecting group R¹'.

14. The method of claim 13, wherein adding the binding unit further comprises adding the binding unit to the amine substituent.

15. The method of claim 11, wherein R⁶ is H.

* * * * *

UNITED STATES PATENT AND TRADEMARK OFFICE
CERTIFICATE OF CORRECTION

PATENT NO. : 7,847,105 B2  Page 1 of 1
APPLICATION NO. : 12/090445
DATED : December 7, 2010
INVENTOR(S) : Sanjeev Gangwar et al.

It is certified that error appears in the above-identified patent and that said Letters Patent is hereby corrected as shown below:

In the Claims:

At column 32, lines 25-38 in the compound of formula (I) of claim 11 of the printed patent, please delete " 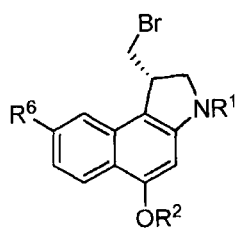 " and add -- 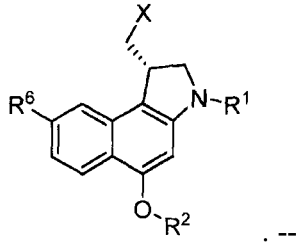 . --

Signed and Sealed this
Twenty-sixth Day of April, 2011

David J. Kappos
*Director of the United States Patent and Trademark Office*